(12) United States Patent
Li

(10) Patent No.: US 10,668,682 B2
(45) Date of Patent: Jun. 2, 2020

(54) SUPPORT AND METHOD FOR ADDITIVE FABRICATION OF FOOT ORTHOTICS

(71) Applicant: SHAOXING OU AI DI MEDICAL TECHNOLOGY CO., LTD., Shaoxing (CN)

(72) Inventor: Yong Li, LaSalle (CA)

(73) Assignee: SHAOXING OU AI DI MEDICAL TECHNOLOGY CO., LTD., Shaoxing, Zhejiang (CN)

( * ) Notice: Subject to any disclaimer, the term of this patent is extended or adjusted under 35 U.S.C. 154(b) by 396 days.

(21) Appl. No.: 15/519,082

(22) PCT Filed: Oct. 6, 2015

(86) PCT No.: PCT/CA2015/051011
§ 371 (c)(1),
(2) Date: Apr. 13, 2017

(87) PCT Pub. No.: WO2016/058091
PCT Pub. Date: Apr. 21, 2016

(65) Prior Publication Data
US 2017/0252981 A1   Sep. 7, 2017

Related U.S. Application Data

(63) Continuation-in-part of application No. 14/638,911, filed on Mar. 4, 2015, now abandoned.
(Continued)

(51) Int. Cl.
*B29D 35/12* (2010.01)
*B29C 64/40* (2017.01)
(Continued)

(52) U.S. Cl.
CPC .............. *B29D 35/12* (2013.01); *A43B 7/141* (2013.01); *A43D 1/025* (2013.01); *A61F 5/0111* (2013.01);
(Continued)

(58) Field of Classification Search
None
See application file for complete search history.

(56) References Cited

U.S. PATENT DOCUMENTS

| 4,749,347 A | 6/1988 | Vlavaara |
| 5,121,329 A | 6/1992 | Crump |

(Continued)

FOREIGN PATENT DOCUMENTS

| EP | 2196173 A2 | 6/2010 |
| WO | 2014014977 A2 | 1/2014 |
| WO | 2014080217 A1 | 5/2014 |

OTHER PUBLICATIONS

Leopoly Ltd., "How to prepare 3D models for 3D printing, from Leopoly to basic desktop printers", FAQ, [online Feb. 21, 2014] [retrieved at <http://leopoly.com/media/2014/02/Leo_3DPrint_FAQ.pdf> on Dec. 9, 2015].
(Continued)

*Primary Examiner* — Jacob T Minskey
*Assistant Examiner* — Baileigh Kate Darnell

(57) ABSTRACT

A method for additive fabrication of foot orthotics comprises printing, in successive layers, a side support; and printing, in successive layers, a foot orthotics on the side support, wherein the foot orthotics comprises a side edge printed directly on top of the side support, and is supported on and connected to the side support through the side edge. A controller for controlling operation of an additive fabrication device comprises a processor and a memory. The memory stores thereon processor-executable-code, the code when
(Continued)

executed by the processor, causes the additive fabrication device to print foot orthotics according to the above method. A method is also provided to construct a data structure for additive fabrication of foot orthotics according to the above. A computer comprising a processor and a memory is provided for constructing such a data structure.

13 Claims, 22 Drawing Sheets

Related U.S. Application Data

(60) Provisional application No. 62/064,285, filed on Oct. 15, 2014.

(51) Int. Cl.

| | | |
|---|---|---|
| *B33Y 10/00* | (2015.01) | |
| *A61F 5/01* | (2006.01) | |
| *A61F 5/14* | (2006.01) | |
| *B33Y 80/00* | (2015.01) | |
| *B33Y 50/00* | (2015.01) | |
| *A43D 1/02* | (2006.01) | |
| *A43B 7/14* | (2006.01) | |
| *B29C 64/386* | (2017.01) | |
| *B29C 64/112* | (2017.01) | |
| *G06F 30/00* | (2020.01) | |
| *G06F 30/20* | (2020.01) | |
| *B29L 31/50* | (2006.01) | |
| *B22F 3/105* | (2006.01) | |
| *G06F 119/18* | (2020.01) | |

(52) U.S. Cl.
CPC ............. *A61F 5/14* (2013.01); *B29C 64/112* (2017.08); *B29C 64/386* (2017.08); *B29C 64/40* (2017.08); *B33Y 10/00* (2014.12); *B33Y 50/00* (2014.12); *B33Y 80/00* (2014.12); *G06F 30/00* (2020.01); *G06F 30/20* (2020.01); *A43D 2200/60* (2013.01); *B22F 2003/1057* (2013.01); *B22F 2003/1058* (2013.01); *B29L 2031/50* (2013.01); *G06F 2119/18* (2020.01); *Y02P 10/295* (2015.11)

(56) References Cited

U.S. PATENT DOCUMENTS

| | | |
|---|---|---|
| 8,538,570 B2 | 9/2013 | Stanhope et al. |
| 8,838,263 B2 | 9/2014 | Sivak et al. |
| 9,183,325 B2 * | 11/2015 | Wighton ................ B33Y 50/00 |
| 10,011,079 B2 * | 7/2018 | Wighton ................ B33Y 50/00 |
| 2014/0303942 A1 * | 10/2014 | Wighton ................ B33Y 50/00 703/1 |
| 2014/3000017 | 10/2014 | Wighton |
| 2015/0165690 A1 * | 6/2015 | Tow ...................... B33Y 80/00 700/119 |
| 2016/0021982 A1 * | 1/2016 | Davis ...................... A43D 5/02 29/559 |

OTHER PUBLICATIONS

Toureztzky, Dave, "15-294 Rapid Prototyping Technologies: Molecule Exercise and Cube Intro", Exercise, Carnegie Mellon University, [online Sep. 20, 2014] [retrieved at <www.cs.cmu.edu/afs/cs/academic/class/15294-f14/lectures/molecule/molecule.pdf> on Dec. 9, 2015].

Airwolf 3D, "Airwolf 3D HD2X, Dual Extruder 3D printer manual", User manual [online], [online Aug. 1, 2014] [retrieved at <http://airwolf3d.com/wp-content/uploads/2014/07/HD2x_Manual1.pdf> on Dec. 9, 2015].

International Preliminary Report on Patentability dated Nov. 17, 2016 in PCT/CA2015/051011.

International Search Report dated Dec. 21, 2015 in PCT/CA2015/051011.

Written Opinion dated Dec. 21, 2015 in PCT/CA2015/051011.

Schall et al., "Robust Filtering of Noisy Scattered Point Data", Eurographics Symposium on Point-Based Graphics (2005) <http://citeseerx.ist.psu.edu/viewdoc/download?doi=10.1.1.88.6853&rep=rep1&type=pdf> retrieved on Jun. 3, 2015.

Zwicker, "Meshing Point Clouds Using Spherical Parameterization", Eurographics Symposium on Point-Based Graphics (2004) <http://graphics.ucsd.edu/~matthias/Papers/MeshingUsingSphericalParameterization.pdf> retrieved on Jun. 3, 2015.

\* cited by examiner

SUPPORT AND METHOD FOR ADDITIVE FABRICATION OF FOOT ORTHOTICS

CROSS-REFERENCE TO RELATED APPLICATIONS

This application is a U.S. National Phase Application under 35 U.S.C. § 371 of International Application No. PCT/CA2015/051011, filed Oct. 6, 2015, entitled SUPPORT AND METHOD FOR ADDITIVE FABRICATION OF FOOT ORTHOTICS, which claims the benefit of, and priority from, U.S. Provisional Patent Application No. 62/064,285, filed Oct. 15, 2014, and U.S. patent application Ser. No. 14/638,911, filed Mar. 4, 2015, the entire contents of each of which are incorporated herein by reference.

FIELD

The present invention relates to method and devices for constructing foot orthotics.

BACKGROUND

Foot orthotics can be fabricated by different techniques. Recently, additive fabrication/manufacturing techniques such as three-dimensional printing (3D printing) techniques have been used to fabricate foot orthotics, including customized foot orthotics. Additive manufacturing technology typically includes various processes to deposit, cure, fuse, or otherwise form layers in sequence to form a three-dimensional (3D) object.

For example, fused deposition modeling (FDM) technique, which is generally disclosed in U.S. Pat. Nos. 4,749,347 and 5,121,329, incorporated here by reference, include melting a filament of build material, extruding the print material out of an extrusion nozzle that is moved horizontally in the X and Y axes to deposit a thin melted and extruded print material on the previous layer where the new layer cools and hardens. These cross-sectional layers are stacked along the Z axis to form the 3D object. Most additive manufacturing processes need a base layer to print the next layer on top of it with a limited overhang.

In a typical 3D printing process, the printed object is supported on a bottom support. For fabrication of foot orthotics, the foot orthotics is typically printed bottom-up and the already printed material is supported from the bottom under the bottom surface of the foot orthotics. The rearfoot and forefoot postings have downward facing planar surfaces and are relatively easy to support. As the arch section of the foot orthotics also needs support, in some techniques, a temporary supporting raft with a curved top is first printed under the arch section of the foot orthotics and the foot orthotics is then printed on top of the supporting raft. The supporting raft and the foot orthotics may be printed with the same printing material, in which case it may be difficult to separate the supporting raft from the printed foot orthotics without leaving some surface defects or flaws on the printed foot orthotics. The supporting raft and the foot orthotics may also be printed with different printing materials, in which case the supporting raft may be more easily removed from the 3D printed foot orthotics, such as by mechanical or chemical means. Discrete supports, such as in the form of pillars or rib arrays, have also been used in some cases.

However, there are a number of drawbacks in such techniques. For example, printing the supporting raft requires both additional printing material and printing time. In some cases, the surface finish on the bottom surface of the resulting product is not smooth. When discrete supports are used, the bottom surface of the foot orthotics has portions that are not in contact with the supports, and these portions can still sag during the printing process. These factors tend to reduce the surface quality, surface finish and dimensional accuracy of the final product, and can increase the production failure rate.

SUMMARY

In an aspect of the present disclosure, a method for additive fabrication of foot orthotics comprises printing, in successive layers, a side support; and printing, in successive layers, a foot orthotics on the side support, wherein the foot orthotics comprises a side edge printed directly on top of the side support, and is supported on and connected to the side support through the side edge. The side edge may be a medial or lateral edge of the foot orthotics. The side support may comprise a base plate and a vertical wall formed on the base plate. The vertical wall may be thinner than a thickness of the side edge of the foot orthotics. The base plate may comprise an elongated central section having a first width, and widened end sections having a second width wider than the first width for stabilizing the side support. Each one of the end sections may be generally T-shaped, or generally circular-shaped. The side support may comprise spaced sections in intermittent contact with the side edge. The side support may be in continuous contact with the side edge.

In another aspect of the present disclosure, a controller for controlling operation of an additive fabrication device comprises a processor and a memory, the memory storing thereon processor-executable-code, the code when executed by the processor, causes the additive fabrication device to print foot orthotics according to the method described in the preceding paragraph. The additive fabrication device may comprise a three-dimensional printer.

In a further aspect of the present disclosure, a method of constructing a data structure for additive fabrication of foot orthotics according to a method described herein. The method of constructing the data structure comprises obtaining a data structure comprising data representing a foot orthotics, the foot orthotics comprising an orthotic top surface, an opposite bottom surface, and side edges extending from the orthotic surface to the bottom surface; and adding to the data structure additional data representing a side support connected to one of the side edges for supporting the foot orthotics during additive fabrication of the foot orthotics based on the data structure. The side edges of the foot orthotics may comprise a medial edge and a lateral edge. The side support may comprise a base plate and a vertical wall supported on the base plate. The vertical wall may be thinner than a thickness of the side edge of the foot orthotics. The base plate may comprise an elongated central section having a first width, and widened end sections having a second width wider than the first width for stabilizing the side support. Each one of the end sections may be generally T-shaped, or generally circular-shaped. The side support may comprise spaced sections in intermittent contact with the side edge. The side support may be in continuous contact with the side edge.

In another aspect of the present disclosure, a computer comprises a processor and a memory, the memory storing thereon processor-executable-code, the code when executed by the processor, causes the processor to construct a data structure according to a method described herein.

In a further aspect of the present disclosure, a computer-readable medium storing thereon computer-executable code, the code when executed by a computer, causes the computer to construct a data structure according to a method of described herein.

An embodiment described in the present disclosure provides a support structure that can minimize the time and material used for fabricating customized foot orthotics by using additive manufacturing technology, and can improve the properties of three-dimensional (3D) printed foot orthotics. In an embodiment of a modelling process, an initial digital customized 3D foot orthotic model is created or generated. A thin-wall support component may be attached to the medial side of the initial foot orthotic model. A base plate may be then attached to the thin-wall component, which may include anti-warping features that prevent warping of the actual thin-wall component after it has been fabricated. The thin-wall component and the base plate may form a temporary support structure during fabrication of 3D foot orthotics from the foot orthotic model with an additive manufacturing device. In a particular embodiment, the same material can be used to print both the support structure and the 3D foot orthotics. The support structure can be mechanically removed from the fabricated foot orthotics after the additive manufacturing process has been completed. In another embodiment, each of the support structure and the 3D foot orthotics may be printed with a distinct material. In a further embodiment, the support structure can be attached to the lateral side of a 3D foot orthotic model. In another embodiment, during an additive manufacturing process, a printing material may be added layer-by-layer, starting from the support structure, then moving up to the medial side of the foot orthotics and finally ending at the lateral side of the orthotic object. In one embodiment, the additive manufacturing process is fused deposition modeling or fused filament fabrication with polypropylene-alike material being used as print material.

BRIEF DESCRIPTION OF THE DRAWINGS

In the figures, which illustrate, by way of examples only, embodiments of this invention.

DETAILED DESCRIPTION

Figure 1:
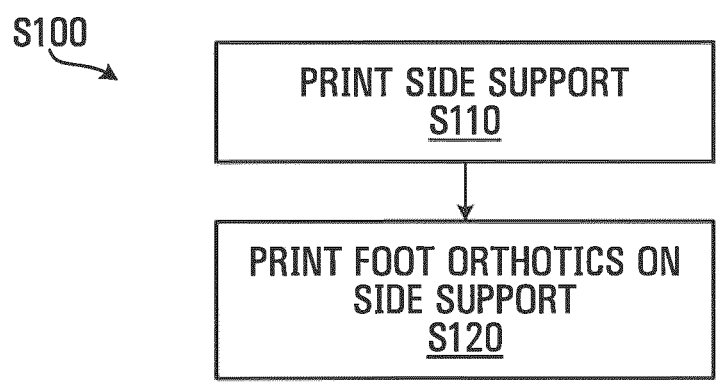
FIG. 1 is a flowchart of a process for additive fabrication of foot orthotics, exemplary of an embodiment of the present disclosure.

In overview, the present disclosure discloses a process for additive fabrication of foot orthotics with a side support. The foot orthotics is supported on the side support during fabrication, with a side edge of the yet-to-be-finished foot orthotics connected to or in contact with the side support. Consequently, the foot orthotics may be fabricated with one of its side edges facing downward and its bottom side facing generally in a horizontal direction.

As compared to using bottom supports to support the foot orthotics from below its bottom surface, using a side support to support the foot orthotics from a side edge can provide one or more benefits, as will become apparent and will be further discussed below.

As used herein, the technical and scientific terms used in the descriptions herein will have the meanings commonly understood by one of ordinary skill in the art, unless specifically defined otherwise.

"Foot orthotic devices" refer to specially designed medical devices or inserts that are worn inside the shoe. Foot orthotic devices may modify or assist foot function. The term "foot orthotics" may be used to refer to foot orthotic devices or electronic models of such devices. As is known in the art, orthotics is concerned with design, manufacture and application of orthoses, which are externally applied devices used to modify structural and functional characteristics of the neuromuscular and skeletal system. For example, foot orthotics may be designed to support specific areas of a foot, to address abnormal foot function or anatomy, or to ameliorate foot pain or other symptoms.

"Top surface" of a foot orthotics refers to the top surface that faces the sole (or plantar surface) of a user's foot when the foot orthotics is worn by the user. "Bottom surface" of the foot orthotics refers to the bottom surface that faces the shoe-bed surface when the foot orthotics is worn by the user. The distance between the top and bottom surfaces of the foot orthotics is referred to as the "thickness" of the foot orthotics.

"Forefoot" refers to the five toes and five metatarsal bones. "Midfoot" refers to the bones of navicular, cuboid, and the three cuneiforms. They form the arch of the foot which serves as a shock absorber. "Rearfoot" is composed of the talus (or ankle bone) and the calcaneus (or heel bone). "Medial arch" refers to the longitudinal arch made up by the calcaneus, the talus, the navicular, the three cuneiforms, and the first, second, and third metatarsals. "Lateral arch" refers to the longitudinal arch made up by the calcaneus, the cuboid, and the fourth and fifth metatarsals. The medial arch is normally higher than the lateral arch.

"Additive manufacturing technology" refers to various processes for making a three-dimensional (3D) object from a 3D model or other electronic data source primarily through additive processes in which successive layers of material are laid down under computer control. The processes include, but not limited to, fused deposition modelling (FDM), stereolithography (SLA), laminated object manufacturing (LOM), electron beam melting (EBM), selective laser sintering (SLS) and inkjet material deposition (IMD). Additive manufacturing technologies may also be known as "3D printing" and additive manufacturing devices may be referred to as "3D printers".

A selected embodiment of the present disclosure is related to a process S100 as illustrated in FIG. 1. In process S100, an additive fabrication system, such as a 3D printer, is used and operated to fabricate foot orthotics layer by layer, such as by a 3D printing technique. At stage S110, a side support is first printed, layer by layer. At stage S120, foot orthotics is printed on the side support layer by layer, with a side edge of the foot orthotics facing down and supported on the side support.

A specific embodiment of process S100 is illustrated with the aid of FIGS. 2A to 2D, which depict schematically the printed objects at different stages of this specific printing process.

Figure 2A:
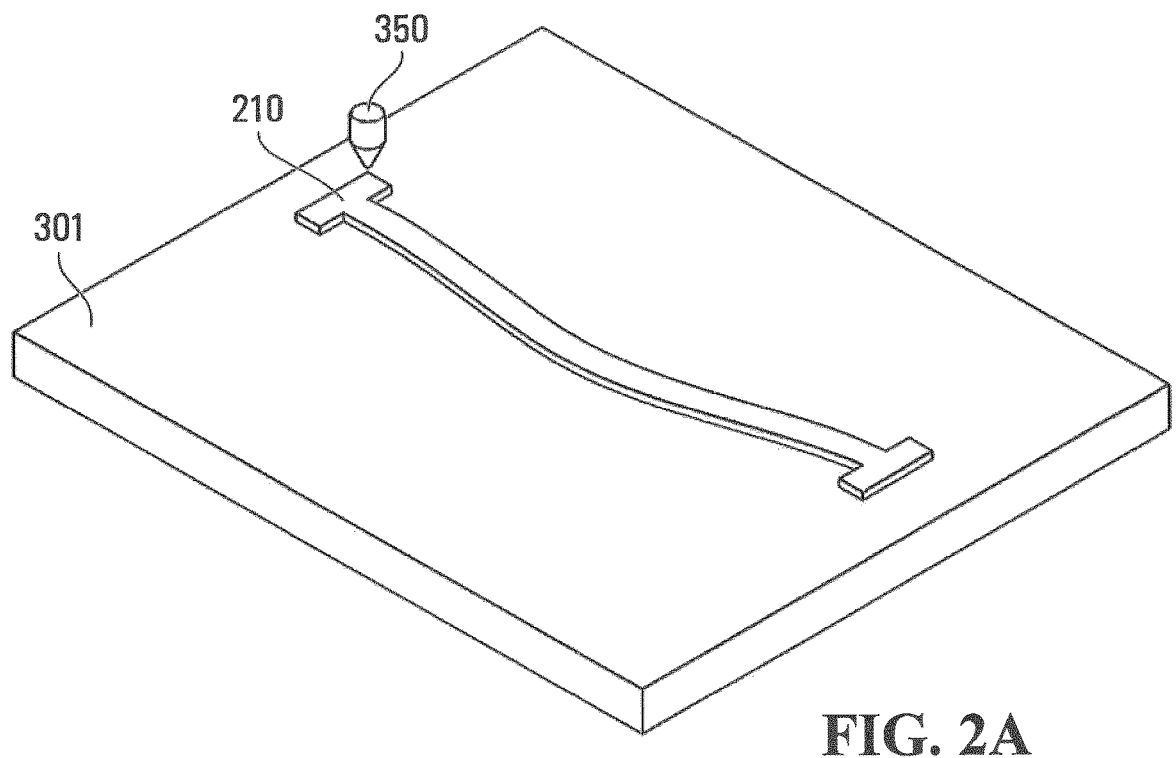
FIGS. 2A, 2B, 2C, and 2D are schematic perspective views of printed objects at different stages in a process of FIG. 1.

Initially, a base plate 210 is printed on a build tray 301 of a 3D printer (not shown in its entirety for simplicity), which is represented by its printer head 350 (or an extrusion nozzle). The printing material is extruded from printer head 350 on to the build tray 301, layer by layer, under control of a printer controller (not shown in FIGS. 2A to 2D) to form the object(s) to be printed. As illustrated in FIG. 2A, base plate 210 has been printed.

Figure 2B:
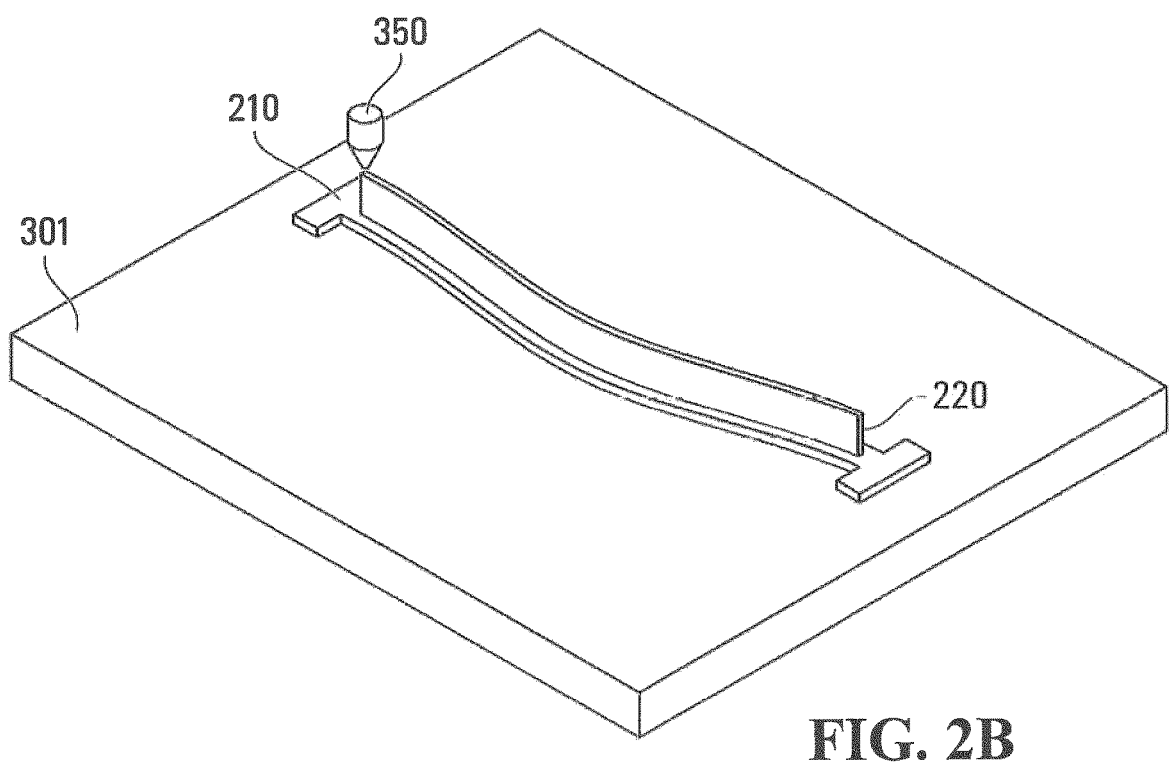

A thin vertical wall 220 is printed on top of base plate 210, as illustrated in FIG. 2B. Vertical wall 220 may be conveniently shaped to correspond to the curvature of the side edge of the foot orthotics to be printed.

Base plate 210 and vertical wall 220 may be continuously printed and form an integrated side support 200.

After side support 200 is at least partially formed, a foot orthotics 250 may be printed on already formed vertical wall 220. In some embodiments, printing of foot orthotics 250 may commence after side support 200 is completely printed, such as when side support 200 is formed with one material and foot orthotics 250 is formed with another material. In some embodiments, printing of parts of foot orthotics 250 may commence once the lowest section of vertical wall 220 has been printed to a suitable height, particularly when side support 200 and foot orthotics 250 are formed with the same material. In the latter case, printing of sections of vertical wall 220 may be completed after a portion of foot orthotics 250 has been printed so that a lower is always finished before the printing head 350 movers up to print the next higher layer. In this regard, it is noted that FIG. 2B depicts a partially printed vertical wall 220. The complete vertical wall 220 can be seen in FIG. 2C, which also shows a partially printed foot orthotics 250.

Figure 2C:
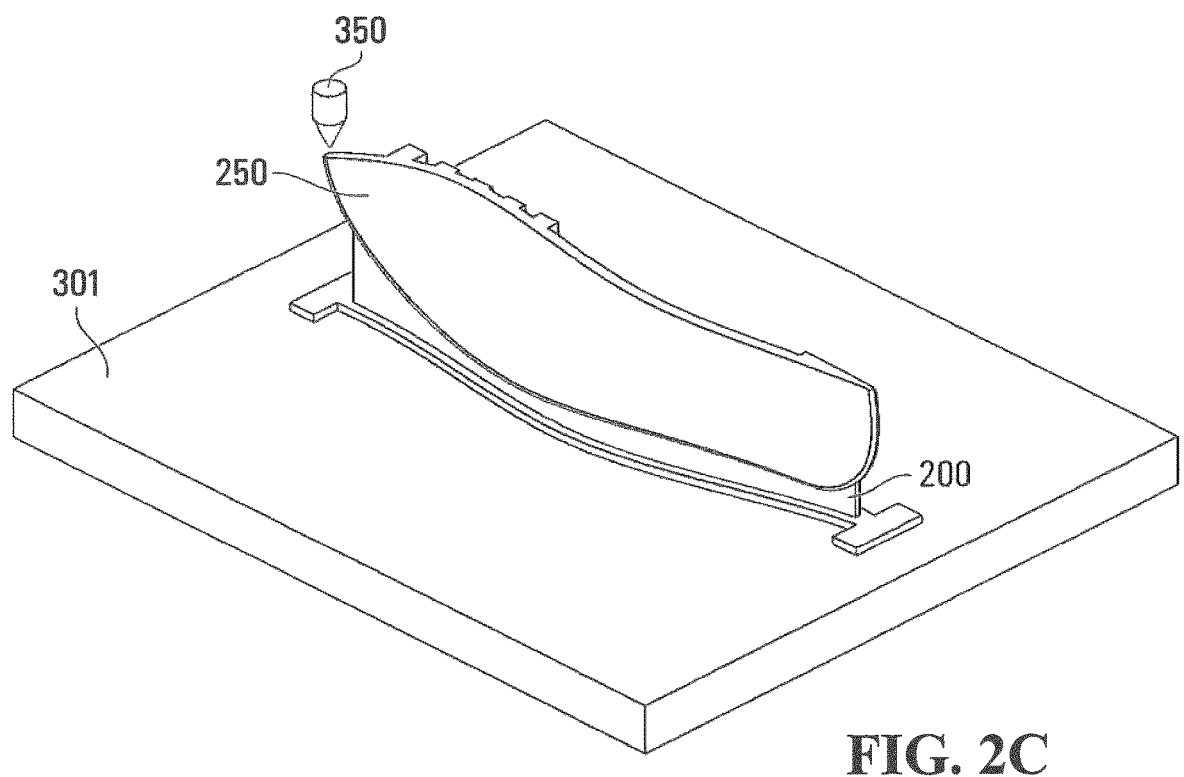
Figure 2D:
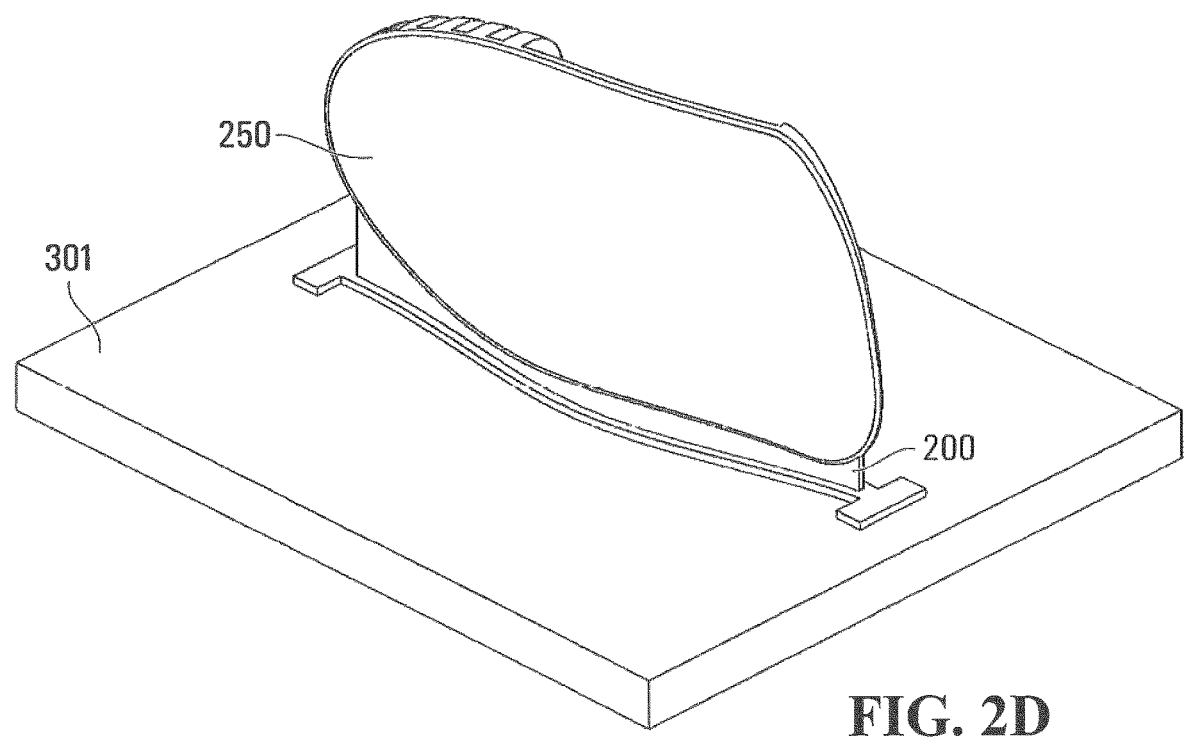

FIG. 2D depicts the completely printed foot orthotics 250. As can be seen, during the printing process, printed portions of foot orthotics 250 is only supported by side support 200, particularly supported on vertical wall 220. The only part of foot orthotics 250 that is directly connected to side support 200 is the side edge (on the lateral side as depicted).

As can be appreciated, foot orthotics 250 is oriented with its top and bottom surfaces facing sideways (i.e. generally horizontally). The side edge of foot orthotics 250 that is facing downward may be the medial side edge, the lateral side edge, the front edge, or the rear edge. In some embodiments, one of medial side or lateral side may be selected as the edge directly supported on side support 200, as this may provide a more stable support, as compared to supporting on the front or rear edge.

Figure 3A:
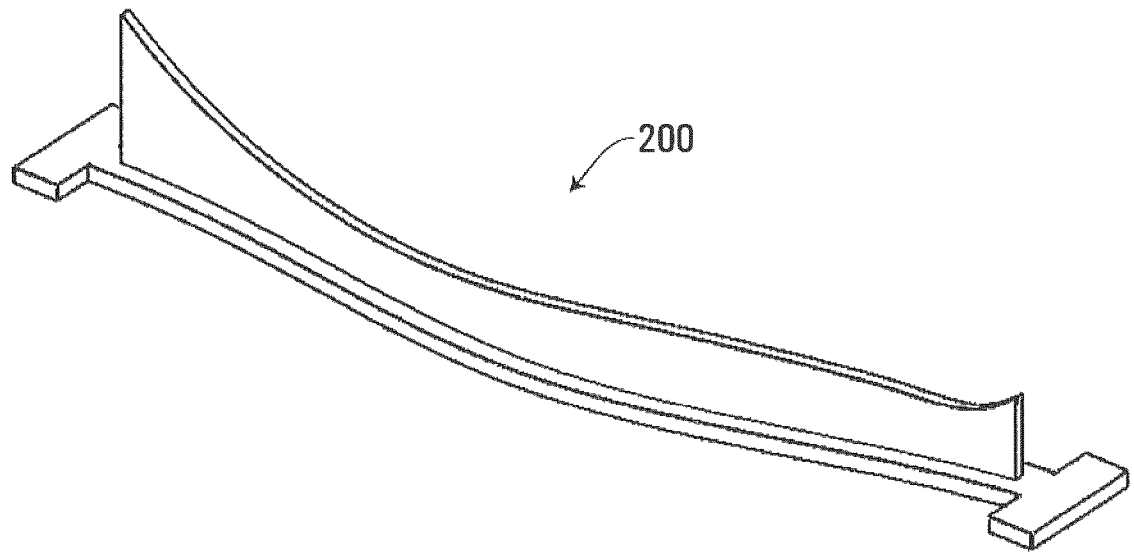
FIG. 3A is a schematic perspective view of a side support in isolation.
Figure 3B:
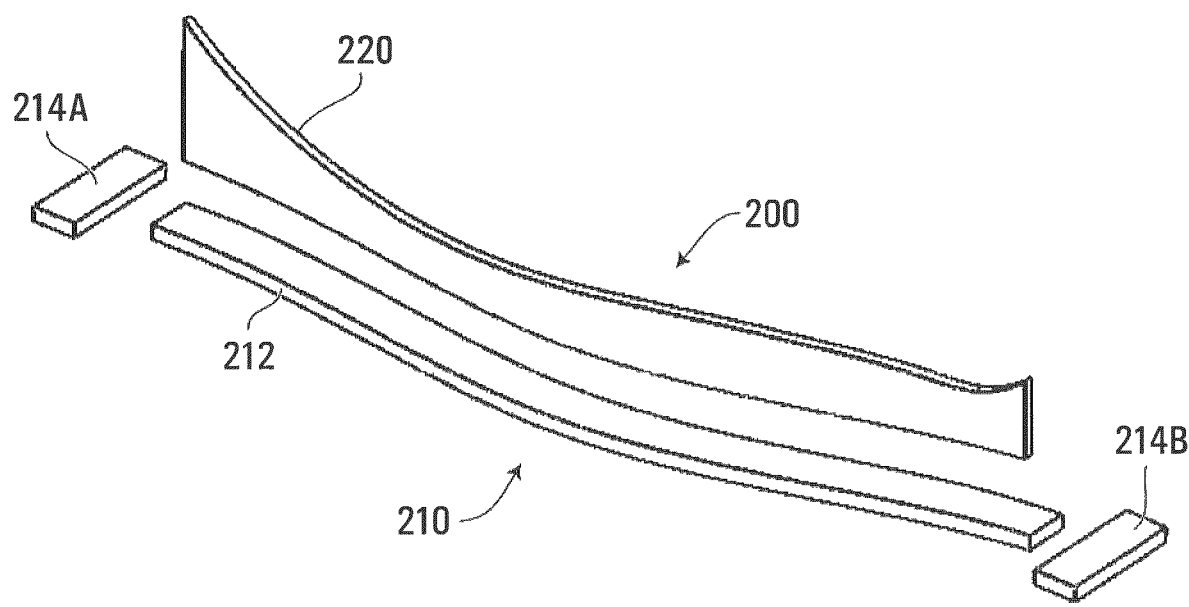
FIG. 3B is a schematic exploded top perspective view of the components of the side support.
Figure 3C:
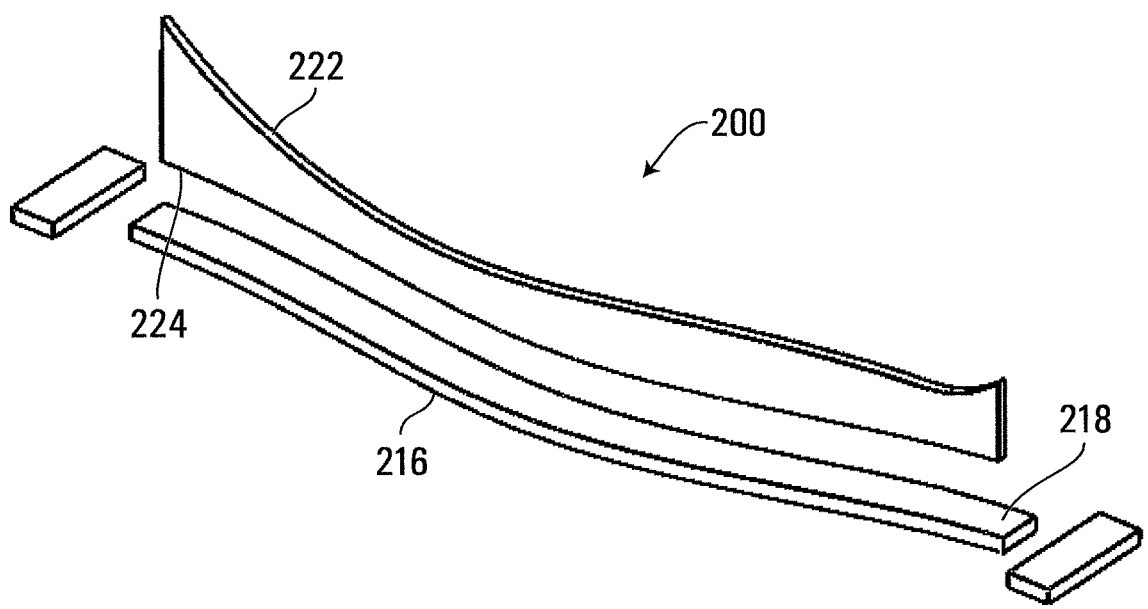
FIG. 3C is a schematic exploded bottom perspective view of the components of the side support.

The structure and construction of side support 200 may be better understood in view of FIGS. 3A to 3C, which depict side support 200 in isolation and in exploded views.

As can be seen, base plate 210 includes an elongated central section 212 and two widened end sections 214A, 214B (the end sections are also collectively or individually referred to as end section 214). Central section 212 and end sections 214A, 214B may have the same thickness, which may be in the range of 0.2 to 10 millimeters. The thickness is selected primarily to ensure the support is stable and will not break down during the fabrication process. Central section 212 is narrower than end sections 214A, 214B in width to reduce material use.

In some different embodiments, base plate 200 may have a uniform width or even a wider central section, but such constructions would require more material to provide the same degree of stability.

As depicted in FIGS. 2A to 2D and 3A to 3C, end sections of base plate 210 are generally T-shaped. In other embodiments, end sections of base plate 210 may have a different shape. For example, the end sections of base plate 210 may have a circular shape (see e.g. FIG. 9J), or another suitable or desired shape.

End sections 214 can serve as anti-warping components to prevent warping of base plate during fabrication. As can be appreciated by those skilled in the art, during some extrusion or 3D printing processes, the just printed material could deform, or warp, before the material is completely solidified and stabilized due to temperature changes and other factors.

Both base plate 210 and vertical wall 220 may be curved. In the depicted embodiment in FIGS. 3A to 3C, vertical wall 220 is a continuous solid object with a continuous top surface 222 and a continuous bottom 224.

In the depicted embodiment, base plate 210 is also a solid object having a flat bottom surface 216 and a flat top 218. Surfaces 216, 218 are generally perpendicular to vertical wall 220. Vertical wall 220 is anchored in the middle of the top surface 216 of base plate 210.

Base plate 210 and vertical wall 220 may be formed integrally or stably connected to form a single object. Different sections or portions of side support 200 may be considered separate parts in concept but in reality may be formed from a continuous and un-separable block of materials.

End sections 214 may be formed of a solid material, and may be formed integrally with central section 212. As noted above, the structure and materials for end sections 214 may be selected to prevent thermal warping and to provide a more stable anchorage for vertical wall 220.

The dimensions, shapes, and materials of side support 200 are selected to provide adequate support for the foot orthotics to be printed, and may vary depending on the size and shape of the foot orthotics to be printed.

Typically, the materials suitable for forming the side support may be selected from materials that are suitable for printing foot orthotics, and materials that are known to be suitable for printing support structures in 3D printing processes. Example materials that may be considered include acrylonitrile butadiene styrene (ABS), polyactic acid (PLA), nylon, high impact polystyrene (HIPS), acrylonitrile styrene acrylate (ASA), polycarbonate (PC), polyphenylsulfone (PPSF or PPSU), high density polyethylene (HDPE), polyethylene terephthalate (PET), thermoplastic elastomers (TPE), other suitable thermoplastic materials, eutectic metals, rubber, modelling clay such as plasticine, metal clay, silicone such as room temperature vulcanization (RTV) silicone, metal alloys, ceramic materials, plaster, photopolymers, or mixtures or combinations thereof. Epoxy resins may be used as printing materials in some embodiments. Powder materials may be used as printing materials in some embodiments. Liquid or solution materials may be used as printing materials in some embodiments. Many suitable printing materials are commercially available and known to those skilled in the art.

For printing side support 200, the printing material may be PLA in some embodiments, or may be water soluble in some embodiments. For instance, water soluble polyvinyl alcohol (PVA) may be used for forming side support 200 in a particular embodiment.

The materials may be printed by any suitable technique such as a suitable extrusion technique. For example, fused deposition modelling (FDM), or a known photo or other curing technique, may be used in the printing process. Other possible techniques include selective laser sintering, direct metal laser sintering, selective laser melting, fused filament fabrication, stereolithography, or the like.

Typical dimensions in some embodiments may be as follows. The length of the side support can range from 50 to 300 millimeters and the width of the side support can be from 5 to 50 millimeters. In an embodiment, one or both of base plate 210 and vertical wall 220 may have a thickness of about 1 mm. In some embodiments, the thickness may vary from about 0.2 mm to about 3 mm. In some embodiments, the thickness may be up to about 10 mm. These embodiments may be suitable when foot orthotics 250 has a typical thickness in the range of about 1.5 to about 10 mm. The minimum height of vertical wall 220 may be about 1 mm in an embodiment, and may be higher or lower in other embodiments. The height of vertical wall 220 may be selected taking into consideration of various factors as can be appreciated by those skilled in the art. For example, the side support generally should be sufficiently rigid and provide adequate stability during the printing process, and can be conveniently separated or removed from foot orthotics 250 after printing.

Given that suitable support is provided, other factors such as costs and printing time may also be considered. For example, a thinner and shorter wall may save material and printing time. A thicker wall is more stable but will need more material and more time to print. To reduce the material and print time needed, different construction of the side support may be used. For example, a hollow wall or an interconnected framework may provide suitable support with less material. The vertical wall may be replaced with interconnected pillars or a wall with windows. See further discussion below.

In some embodiments, the dimensions of side support 200 may be selected based on a balanced consideration of various factors.

Figure 4:
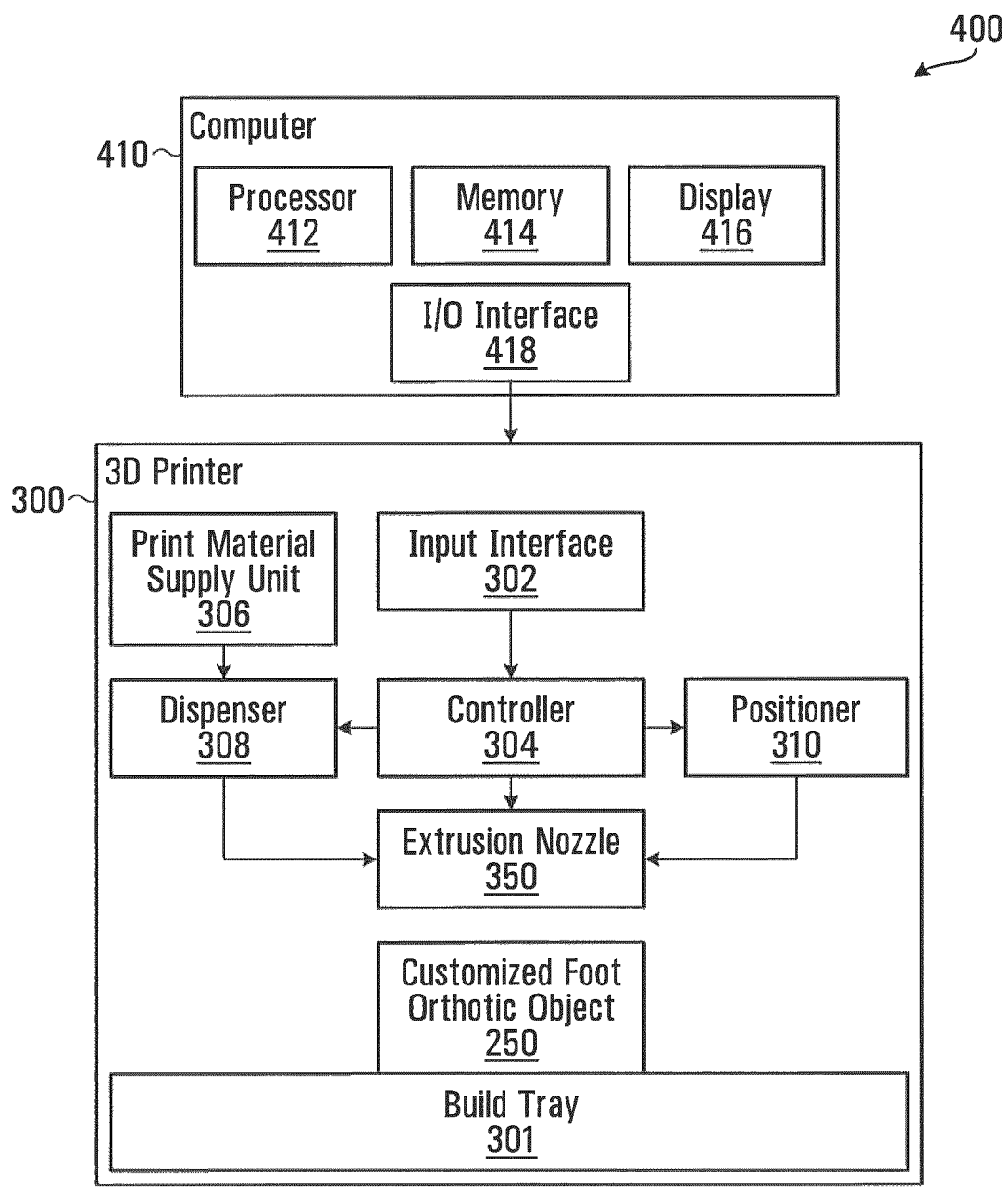
FIG. 4 is a schematic block diagram of a system for additive fabrication of foot orthotics, exemplary of an embodiment of the present disclosure.

In a selected embodiment, process S100 may be carried out using a system 400 as illustrated in FIG. 4.

System 400 includes a computer 410, and an additive fabrication device such as a 3D printer 300.

Computer 410 may include a processor 412, a memory (computer readable medium) 414, display 416, and other input and output (I/O) interfaces 418.

Processor 412 may be any suitable processor or microprocessor, and may be provided as a part of, or in the form of, a central processing unit (CPU).

Memory 414 may be any suitable computer readable medium or storage medium, and may include different and separate devices, such as both transient and persistent memories. Memory 414 may include random access memory (RAM), read only memory (ROM), memory drives or memory disks. Memory 414 may include various computer software and programs stored thereon, which contain computer executable instructions or code for operating computer 410 and performing various functions and tasks as described herein as well as other desired functions and tasks.

I/O interfaces 418 may include any input and output or communication devices or interfaces, which may include input devices or components such as a keyboard, mouse, pointer device, voice input device, data input device, or communication devices including modems, network ports or the like; and output devices such as displays, printers, speakers, storage devices, or communication devices including modems, network ports, or the like.

Various components of computer 410 may be configured and connected in any known and convention manner to perform the necessary or optional functions and task as described here, the details of which are known or can be readily understood or determined by those skilled in the art after reading this disclosure.

Software or programs installed on memory 414 include a program for creating, manipulating and attaching a data structure for a support structure to a data structure for a foot orthotic model.

The digital model may be a computer-aided-drawing (CAD) model of a foot orthotic with a support structure as described herein.

The digital model without the support structure may be created using computer 410 or downloaded from a source to computer 410 in any suitable manner as known to those skilled in the art. The digital model for the support structure may be created using computer 410 with a specially designed software component or a general model design or construction program specifically adapted to produce the support structure as disclosed herein.

Once the digital model for support structure is attached to the foot orthotic model, the combined digital model or data structure may be communicated from computer 410 to 3D printer 420, in any conventional or known manner, such as through I/O interface 418 of computer 410 and input interface 302 of printer 300.

3D printer 300 includes a build tray 301, input interface 302, controller 304, print material supply unit 306, dispenser 308, positioner 310, and extrusion nozzle 350. Other necessary or optional components may be included but are not critical or relevant to the present disclosure, and therefore are expressly shown or further described. In one embodiment, 3D printer 300 may be a FDM 3D printer.

Figure 5:
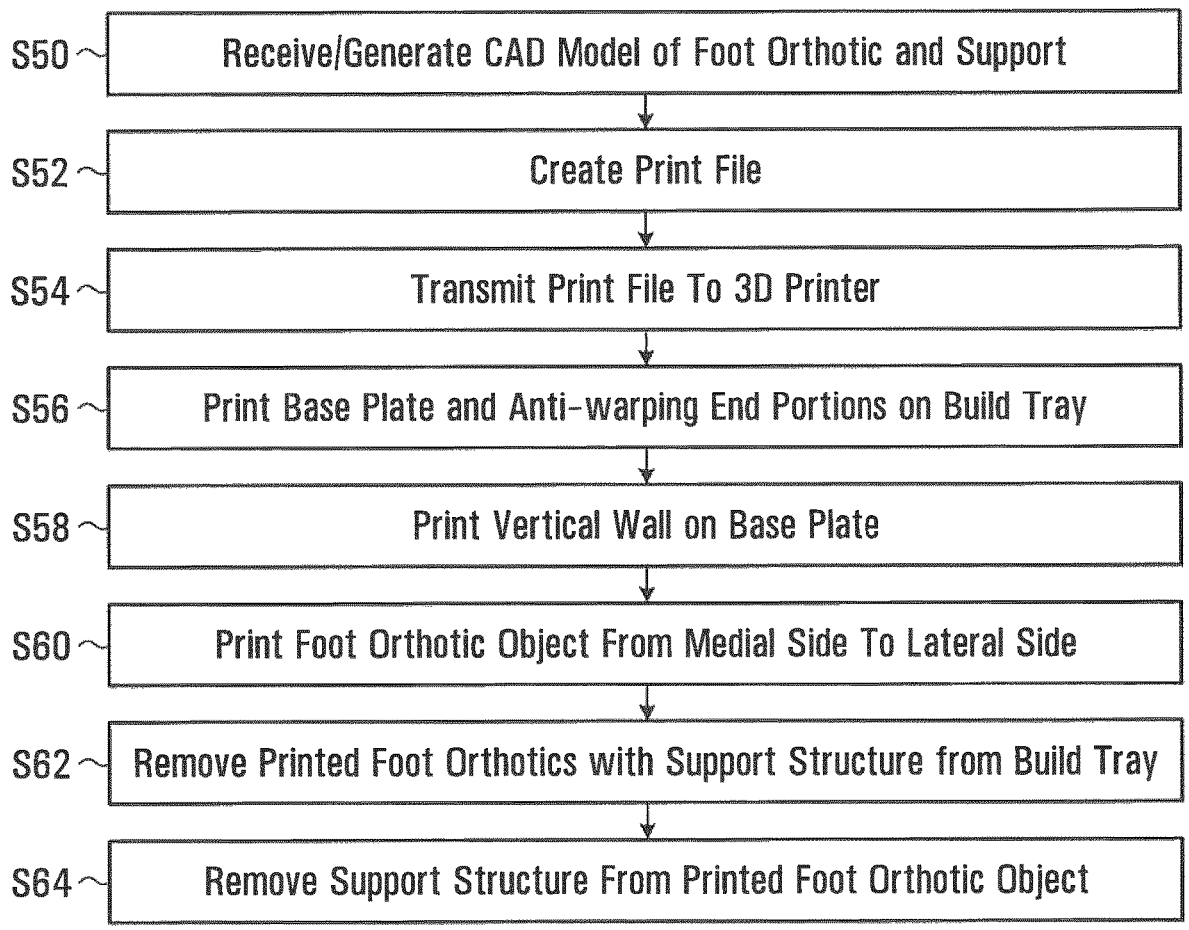
FIG. 5 is a flowchart of a process for additive fabrication of foot orthotics using the system of FIG. 4, exemplary of an embodiment of the present disclosure.

In one embodiment, a physical foot orthotics may be fabricated according to a process as illustrated in FIG. 5.

At stage S50, a CAD model of foot orthotics with disclosed support structure attached is received or created at computer 400.

At stage S52, the CAD model is processed at computer 400 to generate a 3D print file, which is a set of numerical control instructions used to control 3D printer 300 to fabricate the physical foot orthotic object.

At S54, the print file is transmitted to 3D printer 300 via the input interface 302.

At S56, base plate 200 and anti-warping end portions 214 are first printed out on build tray 301 with the bottom surface of base plate 210 facing down and contacting build tray 301 (as illustrated in FIG. 2A).

Build tray 301 is moved by a driving mechanism (not shown) to allow print material be printed and build-up layer by layer during the printing process to allow the extrusion nozzle 350 to print out a new layer on top of the previous layer after the previously is completed.

At S58, the vertical wall 220 is printed out on top of base plate 200 layer-by-layer, completing the side support 200 (as illustrated in FIG. 2B).

At S60, the 3D foot orthotics 250 is printed from its medial side to its lateral side on top of side support 200 (as illustrated in FIGS. 2C and 2D). In different embodiments, a foot orthotics may be printed from its later side to its medial side.

After the 3D printing process is complete, 3D printed foot orthotics 250 object is still supported on and attached side support 200, as illustrated in FIG. 2D.

As is known, the layer thickness in a 3D printing process is an adjustable parameter. In one embodiment, the layer thickness may be 0.2 mm.

The materials suitable for 3D printing foot orthotics may be selected from nylon, polyester, nylon polyester blend, polyethylene, polypropylene, acrylonitile butadiene styrene, polyethylene terephthalate, thermoplastic elastomers, polylactic acid, polycarbonate, rubber, foam rubber, ethylene vinyl acetate, fiberglass, or carbon fiber graphite:

The disclosed support structure and the 3D foot orthotic model can be built by using the same material. However, the disclosed support structure and the 3D foot orthotic model can be built by using different materials or the combination of different materials, respectively.

Figure 6:
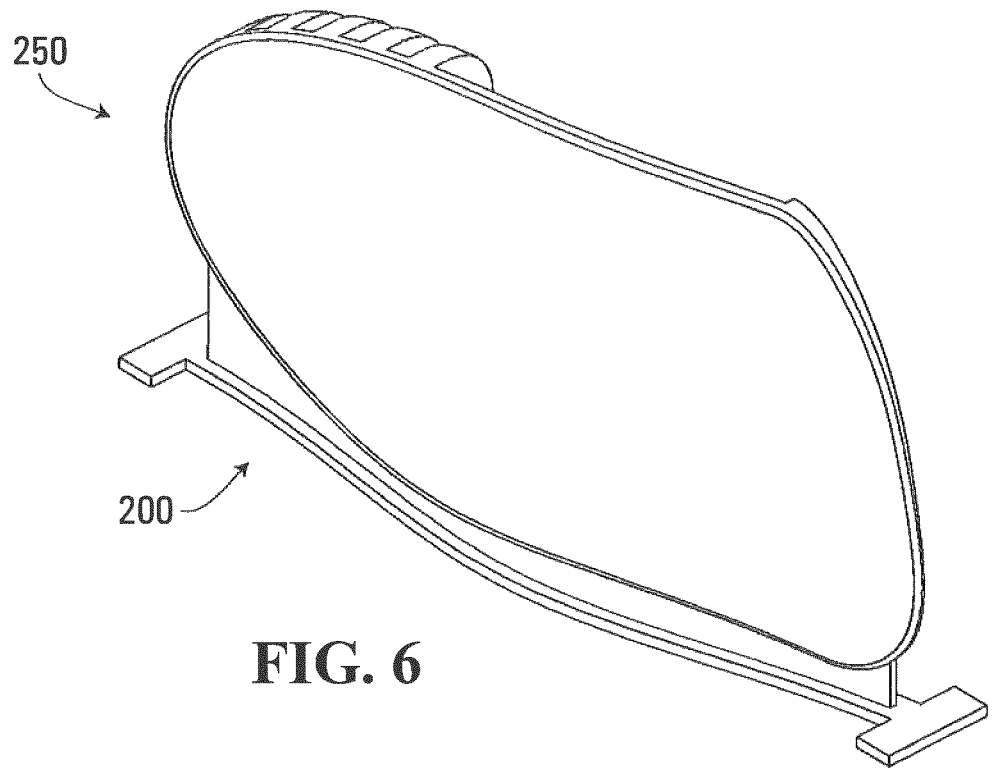
FIG. 6 is a perspective view of a foot orthotics with side support detached from the build tray of a 3D printer.

At S62, the printed foot orthotic object 250 and the side support 200 may be removed together from build tray 301. The removed object is illustrated in FIG. 6.

Figure 7:
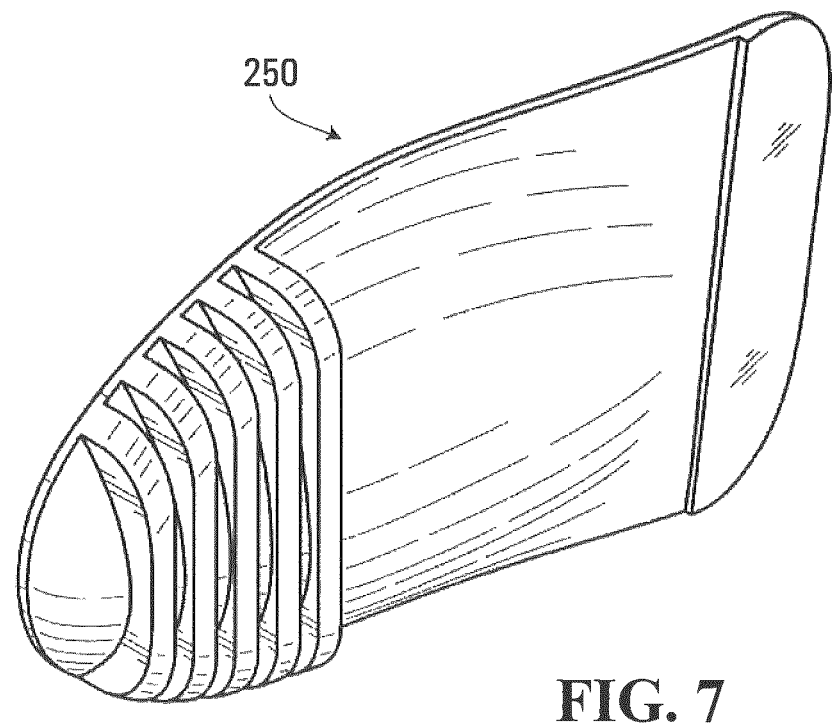
FIG. 7 is a perspective view of the foot orthotics of FIG. 6, separated from the side support of FIG. 6.

At S64, side support 200 may be mechanically separated from foot orthotics 250, such as by grinding. The final foot orthotics 250 separated from side support 200 is illustrated in FIG. 7. A cushioning top-cover can be optionally added on foot orthotics 250 by using an adhesive, which concludes the process.

An advantage of using a side support and print the foot orthotics on the side support sideways is that the support structure may require less amount of material as compared to printing the foot orthotics in a conventional manner.

For example, test results show that, printing a foot orthotics with the sole of the foot orthotics facing down, the support structure required about 38 grams of print material and 88 minutes of printing time. In comparison, when the same foot orthotics was printed sideways on a side support as described above, the side support only required about 6 grams of print material and about 12 minutes of printing time. The tested foot orthotics itself required about 50 grams of print material, which is typical.

The disclosed support structure is only attached to the medial or lateral side of the foot orthotics with a thickness less than few millimeter and the majority of surfaces on the foot orthotic has nothing attached to. The removal of the disclosed support structure by grinding takes about five minutes and leaves almost un-noticeable marks on the foot orthotic object. The disclosed support structure makes it possible for a foot orthotic to be printed in such a unique way that can minimize the time and material for printing and also improve the surface finish, quality of the 3D printed foot orthotics For illustration purposes, it is assumed that a customized three dimensional (3D) foot orthotics will be physically fabricated based on a digital model of the foot orthotics, which may be a computer-aided-design (CAD) model. However, other formats or techniques may be used for controlling fabrication (e.g. printing) of the physical device.

Typically, original CAD models of foot orthotics are for foot orthotics only and don't have any information on a support structure. The disclosed support structure is created and attached to the computerized CAD model of a foot orthotic first. After being created and attached, the disclosed support structure is integrated with the CAD model of foot orthotics. In one embodiment both the support structure and the foot orthotic are saved into a single CAD model file, which is transferred to a 3D printer to physically fabricate the support structure and the foot orthotic object together.

Figure 8:
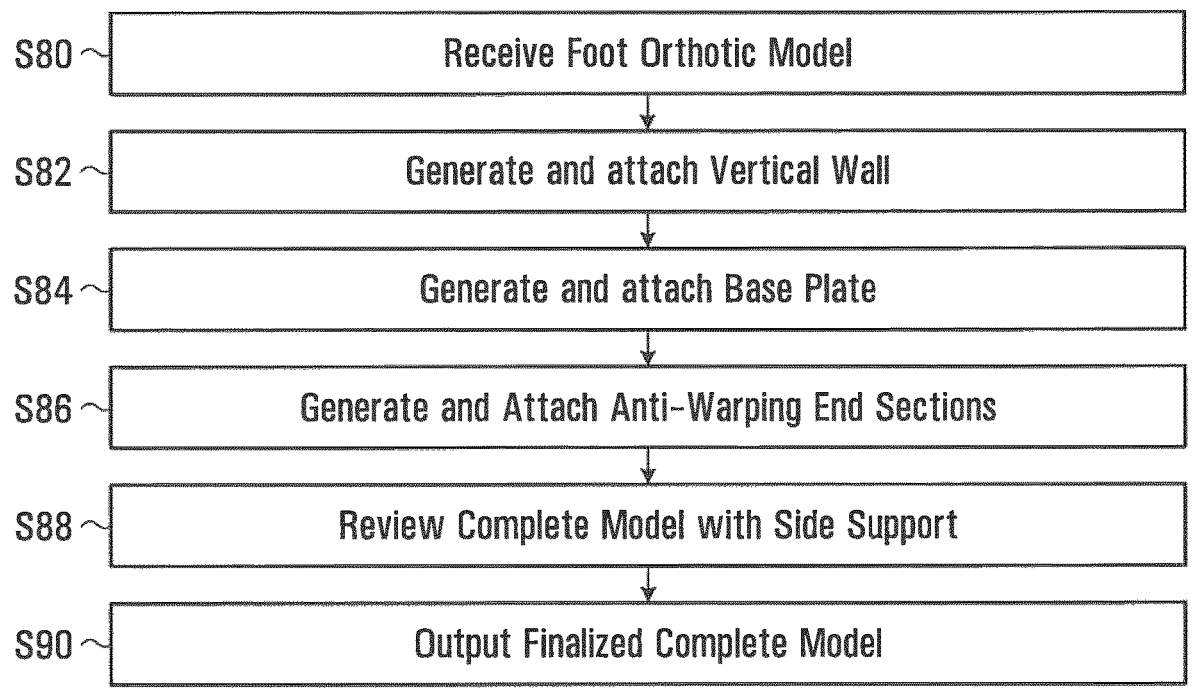
FIG. 8 is a flowchart for attaching data structure of a side support to the data structure of a foot orthotic model.

The procedure of creating and attaching a data structure or model for a side support to a foot orthotic model may include the following stages as shown in the flowchart of FIG. 8.

At S80, the CAD model of foot orthotics 250 is received at computer 400. Suitable processing software or programs may be installed on computer 400 for processing and manipulating the CAD models and other graphics digital data structures. For example, various libraries for modelling and interrogation of curves and surfaces and other 3D shapes and objects, and 3D modelling and numerical simulation programs may be installed. In selected embodiments, the SISL Library (SINTEF, Norway) and OPEN CASCADE™ Technology software modules v.6.6 (OPEN CASCADE SAS, Guyancourt, France) may be used for these purposes. When such programs are installed, the foot orthotic model may be received by these programs running on computer 400 as input data, and the data structure for side support 200 may be created and attached to the foot orthotic model using these programs. Specially designed and programmed software routines may be used to automate such processes.

Other suitable software packages known to those skilled in the art may also be used in this process.

For illustration purposes, it is assumed in the present example that the side support is attached to the medial side of the 3D foot orthotic model. From the present disclosure, a person skilled in the art would readily understand how to attach the side support to the lateral side of the foot orthotic model.

Figure 9A:
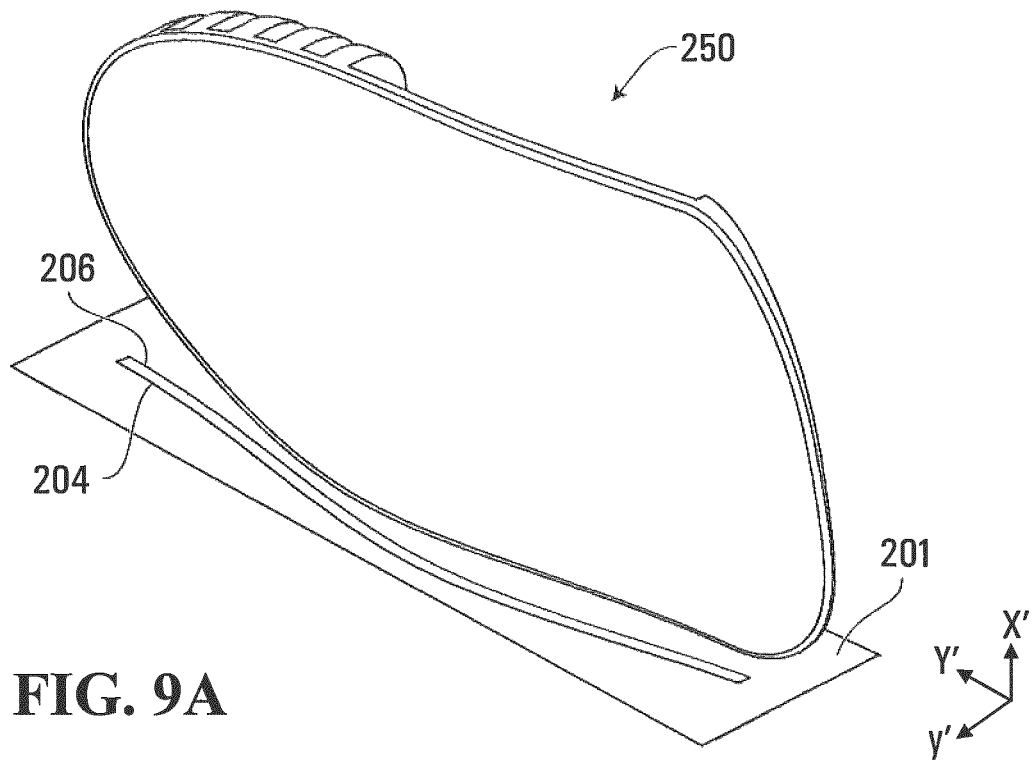
FIG. 9A is a perspective view of a foot orthotic model projected onto a reference plane for forming a profile of a support wall.

At S82, and with further reference to FIG. 9A, a reference plane 201 is generated, which is along the foot length direction and about five to ten millimeters away from the medial side. Reference plane 201 is perpendicular to the rear-foot posting planar surface. The top edge on the medial side of the foot orthotics is projected onto plane 201 to form curve 204. The bottom edge on the medial side of the foot orthotics is projected onto plane 201 to form curve 206. Curves 204 and 206 can be offset and closed on both ends to form a closed base profile, which is then extended upwards, towards the foot orthotics to form the digital profile for the curved vertical wall 220. The extension terminates when the vertical wall profile comes into full contact with the medial side of the foot orthotic model.

The process may include identify the medial side outline points of the orthotic model, create a reference plane for the vertical wall, project the medial side outline points of the orthotic model onto a reference plane, form the vertical wall by pairing the projected outline points and the original outline points. From the outline points on the medial side of the orthotic model, find the "x_max" value and the reference plane is set at X=x_max+margin (or X=Xref), which is perpendicular to the X axis. The margin may be set to about 8 mm. For example, the outline points on the medial side of the orthotic model may have a data structure as shown below:

|   |   |   |
|---|---|---|
| 20.253 | 45.834 | 5.672 |
| 21.134 | 46.241 | 6.154 |
| 22.661 | 46.725 | 6.802 |
| 23.382 | 47.352 | 7.406 |
| 24.801 | 47.889 | 7.952 |
| 25.520 | 48.334 | 8.561 |
| ... | ... | ... |

After the points are projected onto the reference plane (X=Xref), the outline points may have a data structure as shown below.

|   |   |   |
|---|---|---|
| Xref | 45.834 | 5.672 |
| Xref | 46.241 | 6.154 |
| Xref | 46.725 | 6.802 |
| Xref | 47.352 | 7.406 |
| Xref | 47.889 | 7.952 |
| Xref | 48.334 | 8.561 |
| ... | ... | ... |

The base plate 210 may be produced as follows, assuming an offset of about 2 millimeters. The projected outline points are offset in an outward direction on the reference plane. The offset outline points in the X axis are expanded outwards to produce a thickened section to form the base plate.

Figure 9B:
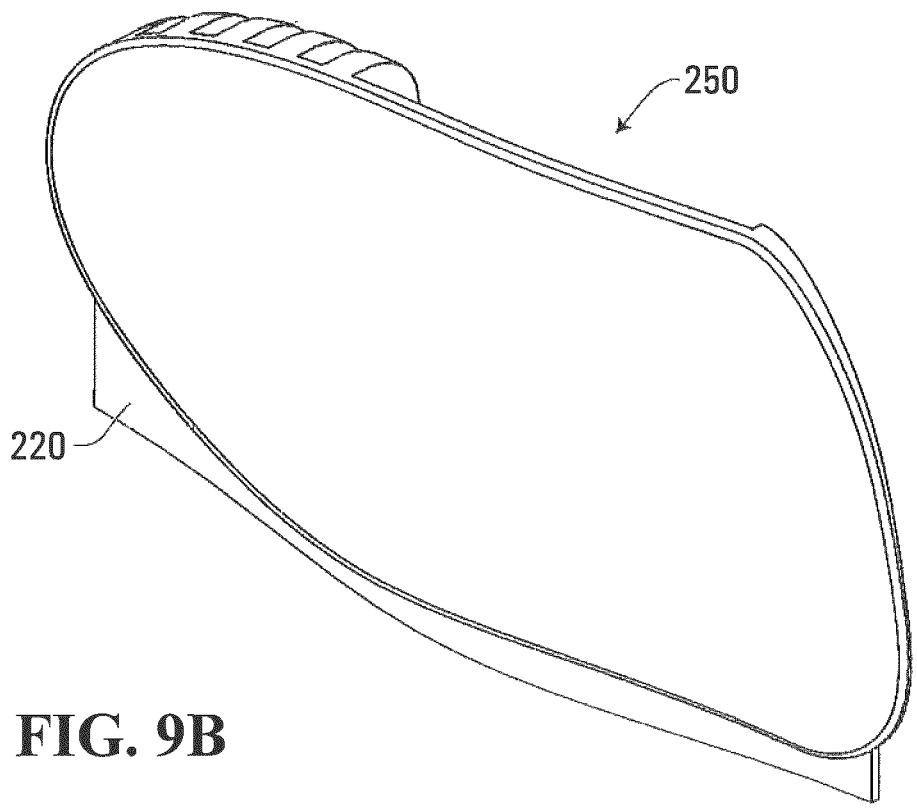
FIG. 9B is a perspective view of the foot orthotic model of FIG. 9A with the generated support wall.

As illustrated in FIG. 9B, after merging of the data structures, a vertical wall profile is attached to the medial side of the foot orthotic model for foot orthotics 250.

Figure 9C:
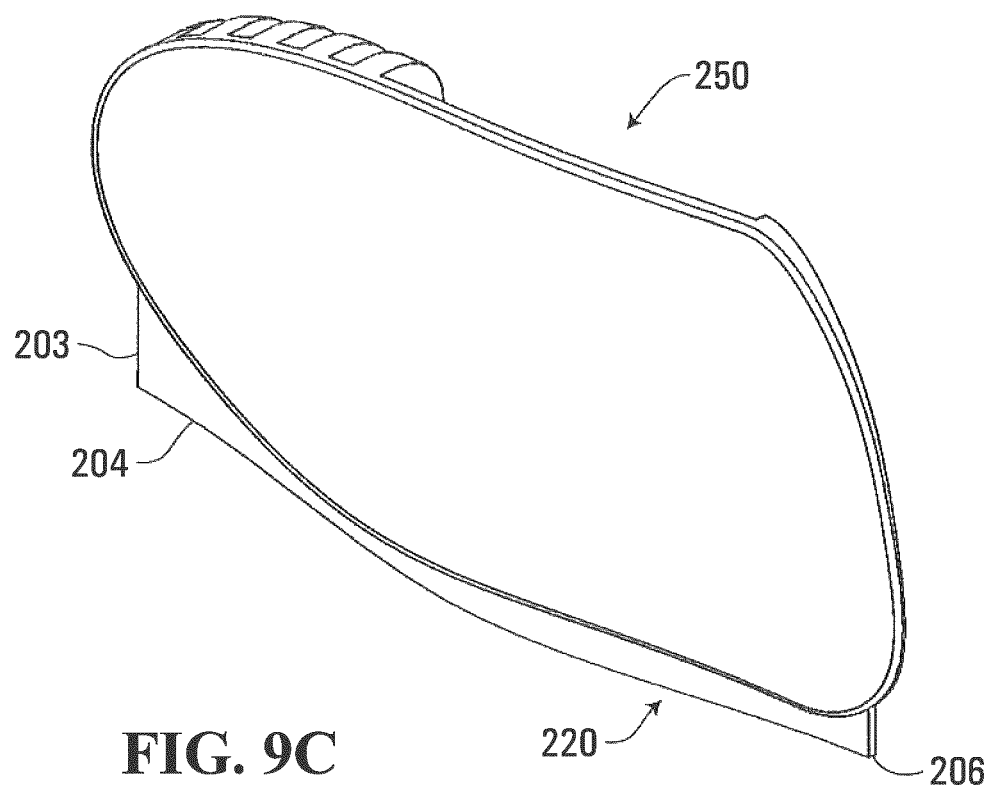
FIG. 9C is another perspective view of the foot orthotic model and support wall of FIG. 9B.

As illustrated in FIG. 9C, the profile of vertical wall 220 has a vertical surface 203, and edges 204 and 206.

Figure 9D:
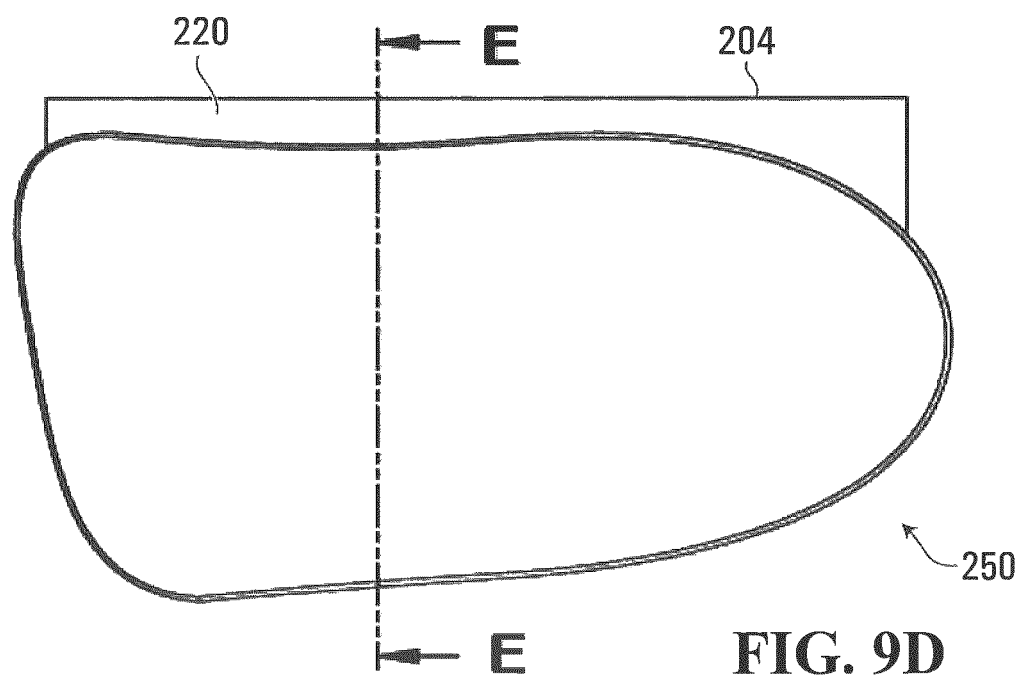
FIG. 9D is a top view of the foot orthotic model and support wall of FIG. 9B.
Figure 9E:
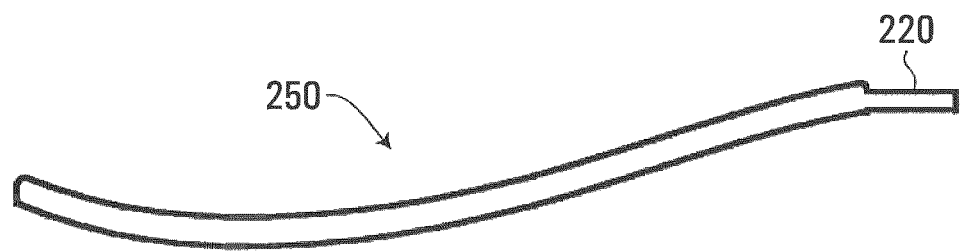
FIG. 9E is a cross-sectional view of the foot orthotic model and support wall of FIG. 9D, taken along lines E-E.

FIG. 9D shows a schematic side view of a 3D foot orthotic model 250 (for a left foot as depicted) with attached vertical wall profile. FIG. 9E shows a schematic cross-sectional view of taken along line AA in FIG. 9D.

In one embodiment, vertical wall 220 may have a thickness of 0.2 to 5 mm. The thickness of vertical wall 220 may be typically less than the thickness of the thinnest portion(s) of the side edges of foot orthotics 250. In some cases, vertical wall 220 may be thicker than the thickness of a side edge of foot orthotics 250. Vertical wall 220 may have a uniform thickness, or may have a varying thickness.

In any event, the profile of vertical wall 220 may match or correspond to the curved profile of the medial side of foot orthotics 250.

As depicted in FIG. 9D, the rear end of vertical wall 220 may be in the heel section of foot orthotics 250 and the front end of vertical wall 220 may be in the first metatarsal head area of foot orthotics 250.

As depicted, vertical wall 220 may be shorter than foot orthotics 250, and may have a minimum height of 5 to 10 mm.

Returning to FIG. 8, at S84, the base portion of the digital profile of vertical wall 220 (interception at reference plane 201) is expanded to generate the top surface boundary profile for base plate 210.

Figure 9F:
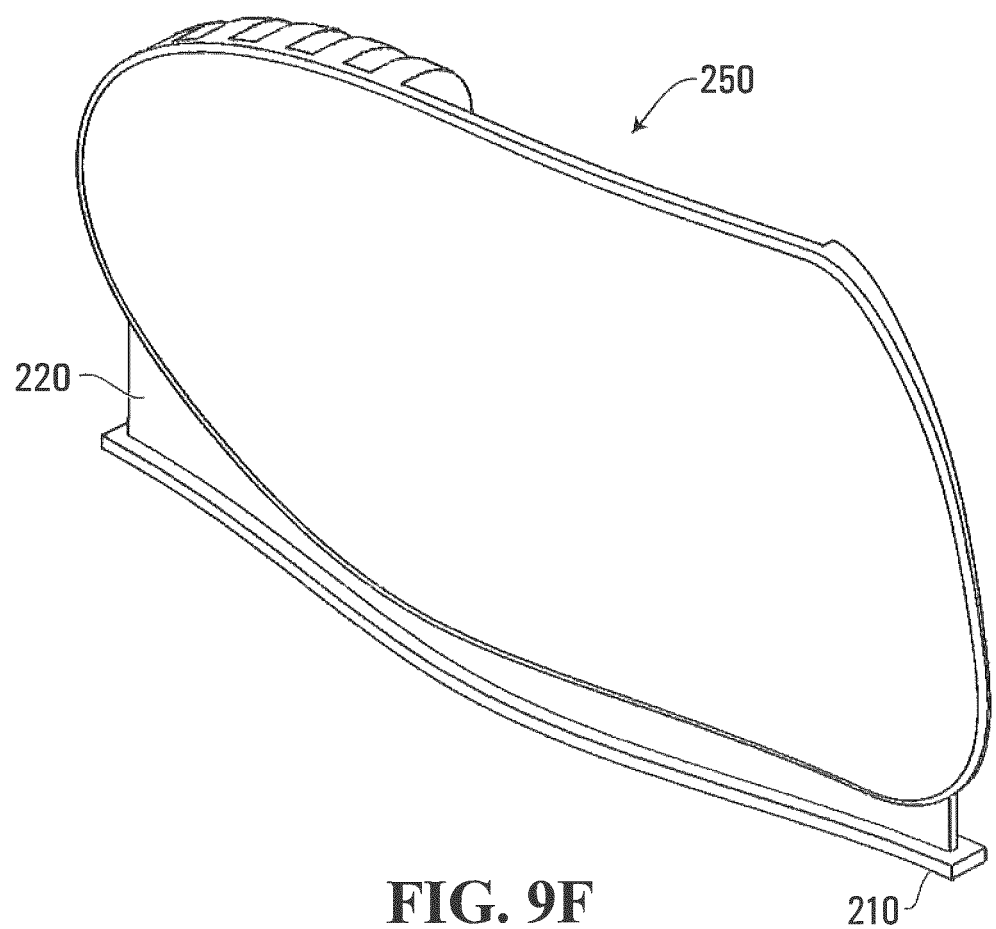
FIG. 9F is a perspective view of the foot orthotic model of FIG. 9A with attached support wall and base plate.
Figure 9G:
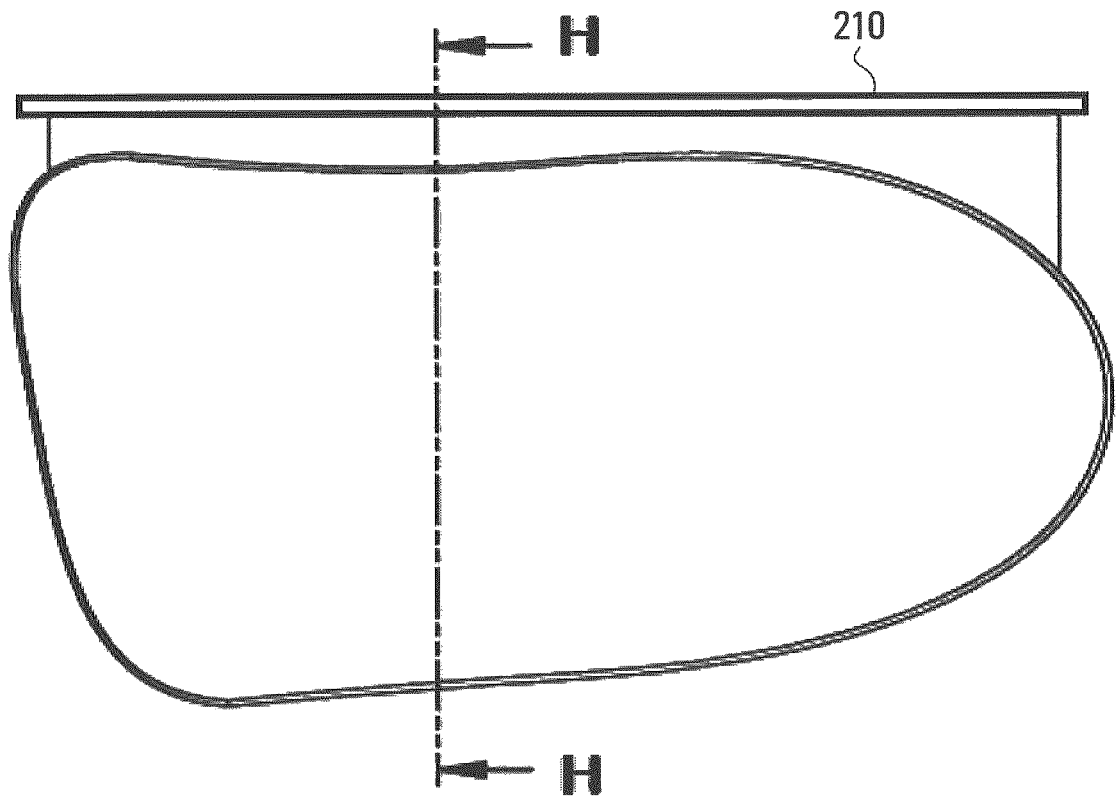
FIG. 9G is a top view of the foot orthotic model of FIG. 9F with attached support wall and base plate.
Figure 9H:
FIG. 9H is a cross-sectional view of the foot orthotic model, support wall, and base plate of FIG. 9G, taken along lines H-H.

The top surface of base plate 210 is kept perpendicular to vertical surface 203 of vertical wall 220. The digital profile for central section 218 of base plate 210 may be first generated as illustrated in FIG. 9F. The cross-sectional view shown in FIG. 9H is taken along lines HH in FIG. 9G.

Base plate 210 may have a height (thickness) that is more than three times of the thickness (width) of vertical wall 220. The width of base plate 210 may be about 2 mm, and the length of base plate 210 may be the same as, or longer than, the length of vertical wall 220.

Due to the internal stress generated by solidification and cooling of print material during printing, a 3D-printed object may deform during or after 3D printing. For example, it may be anticipated that the ends of base plate 210 may deform such as due to what is known as "lifting" or "warping" of the end sections of base plate 210. To prevent or reduce such lifting and warping, an anti-warping component may be used in selected embodiments.

For example, an enlarged section may be provided at each end of base plate 210 to minimize deformation during or after the 3D printing process.

Thus, at S86, digital profiles for anti-warping end sections are generated and attached to the digital profile for base plate 210. Example end sections are illustrated in FIGS. 9I, and 9J.

Figure 9I:
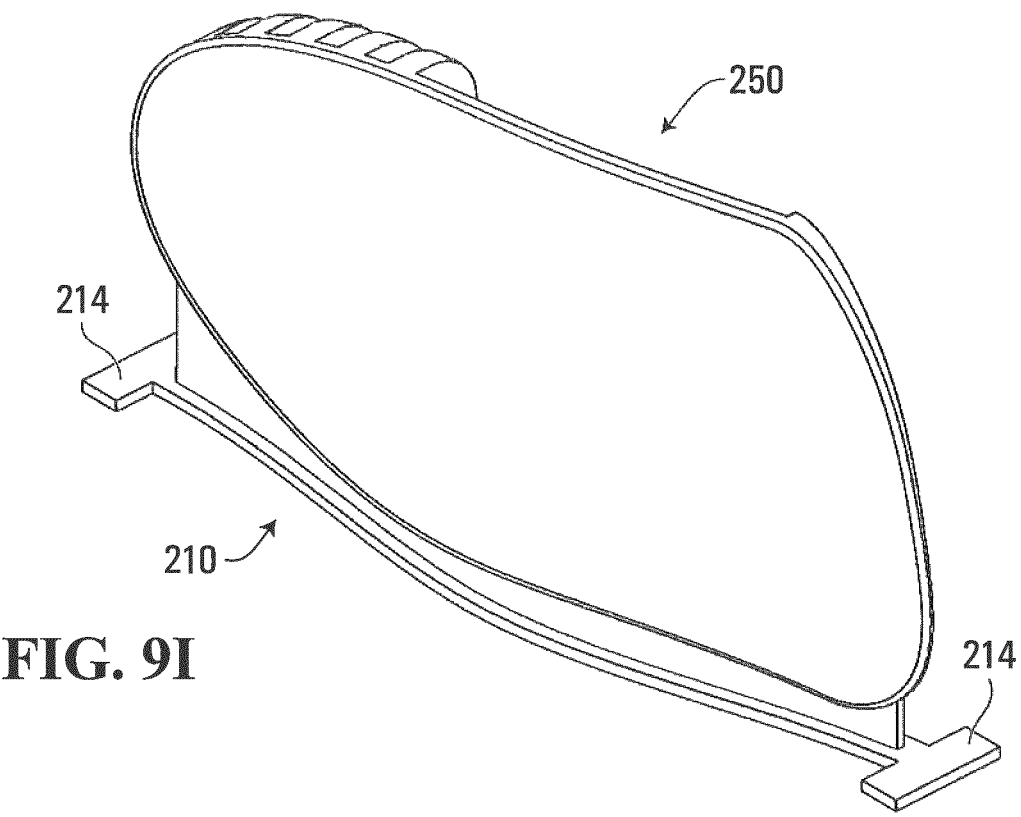
FIG. 9I is a perspective view of the foot orthotic model of FIG. 9A with attached support wall, base plate, and anti-warping end sections.
Figure 9J:
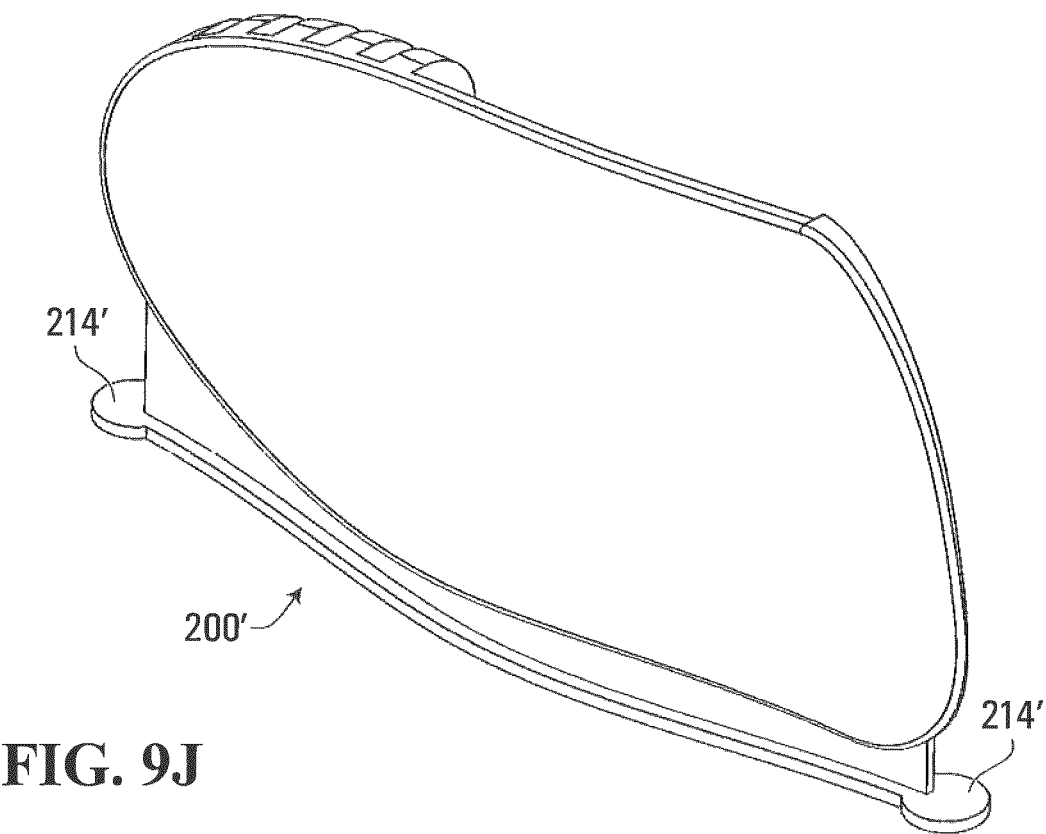
FIG. 9J is a perspective view of the foot orthotic model of FIG. 9A with attached support wall, base plate, and alternative anti-warping end sections.

An end section 214 may have a generally rectangular shape or profile as illustrated in FIG. 9I. In an embodiment, the rectangle for a rectangular end section may be about 17 mm long, about 6 mm wide, and about 2 mm tall (thick). End sections 214 may provide more contact areas with the build tray, and may help to hold base plate 210 in place and attached to build tray 301.

In some embodiments, end sections 214 may have different shapes or profiles. For example, generally circular-shaped or disk-shaped end sections 214' may be provided as illustrated in FIG. 9J. For the purpose of illustration, side support 200' is depicted as attached to the lateral side of foot orthotics 250.

At S88, the complete digital model for foot orthotics 250 with attached side support 200 may be viewed on display 416 for viewing, and editing if necessary or desired.

At S90, the finalized complete model or data structure for foot orthotics 250 with attached side support 200 is output. The output may include outputting the data structure to a 3D printer for printing, or storing the data structure for later use, or transmitting the data structure to another device or location for processing. The output may be provided as a single CAD file suitable for use in a 3D printer. In another embodiment, the data structures for orthotics 250 and side support 200 may also be saved in two or more separate CAD files, and may be transmitted separately, to a 3D printer or another device or user.

As can be appreciated, vertical wall 220 may be a solid wall, or may have openings thereon to reduce the print material used without materially affecting its integrity and strength for supporting foot orthotics 250.

Figure 10A:
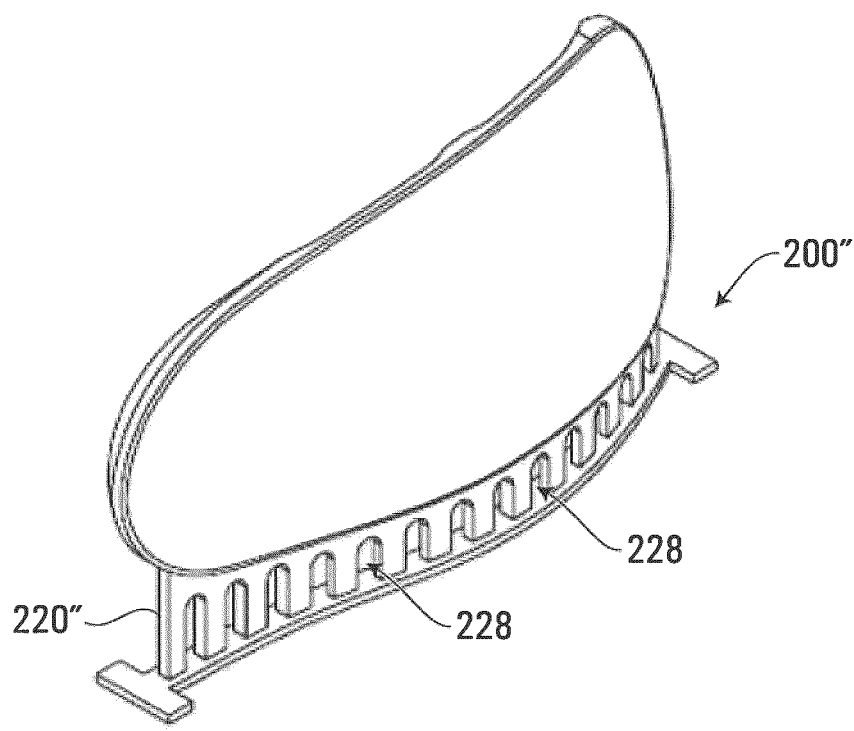
FIGS. 10A and 10B are perspective views of a foot orthotics supported on a side support with openings in the vertical wall of the side support.
Figure 10B:
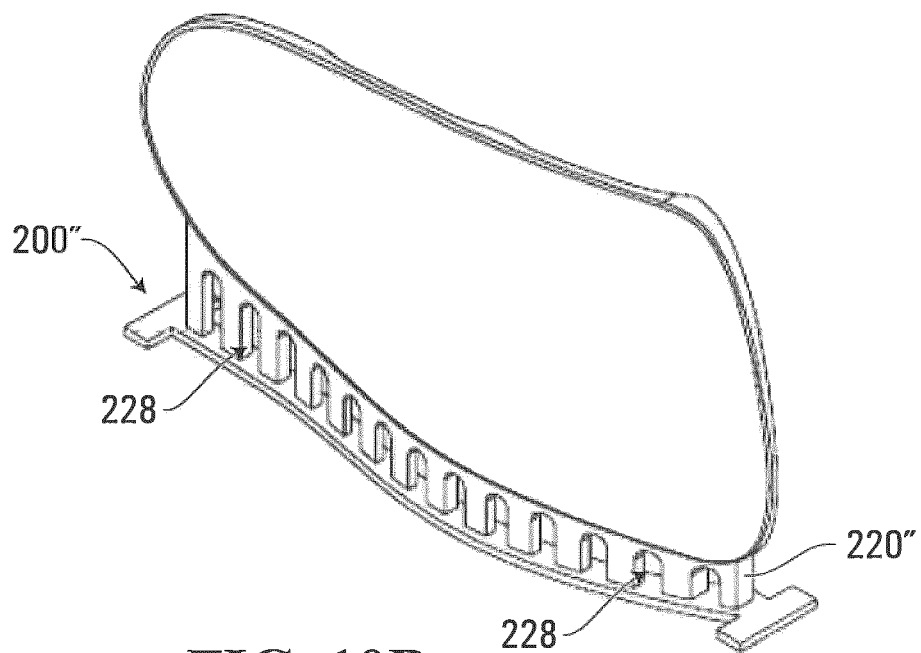
Figure 10C:
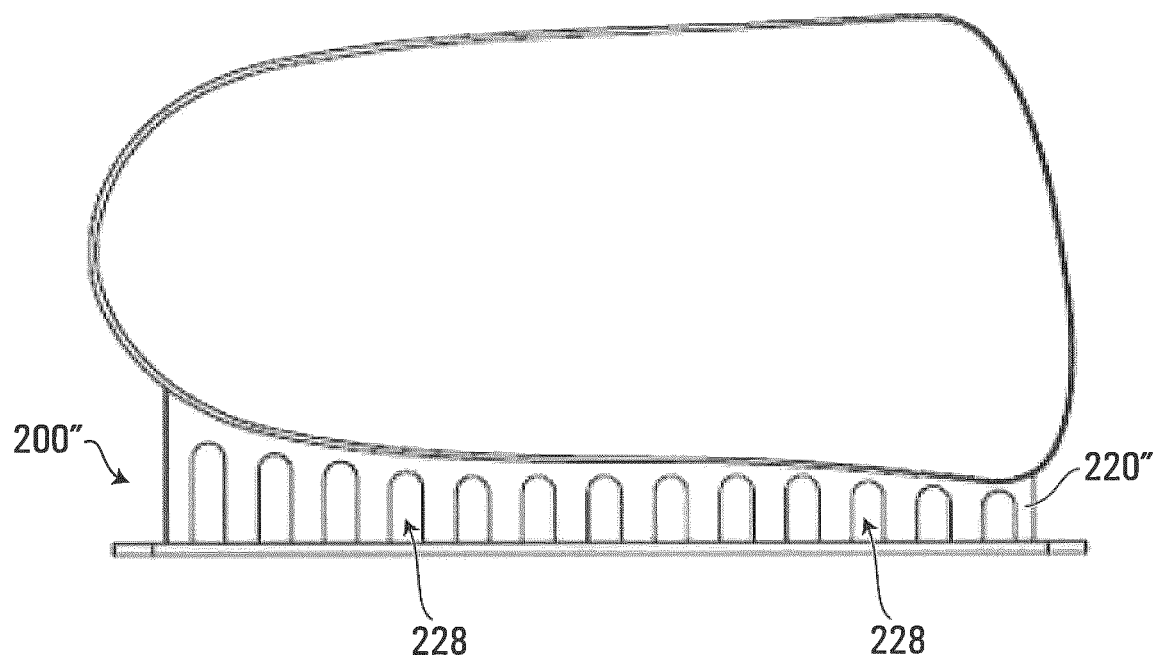
FIG. 10C is side view of the foot orthotics and side support of FIGS. 10A and 10B.

For example, an example side support 200" with a vertical wall 220" having openings 228 is illustrated in FIGS. 10A to 10C. Other types of vertical support, such as an interconnected framework or pillars (not shown), may also be suitable depending on the application.

Figure 11:
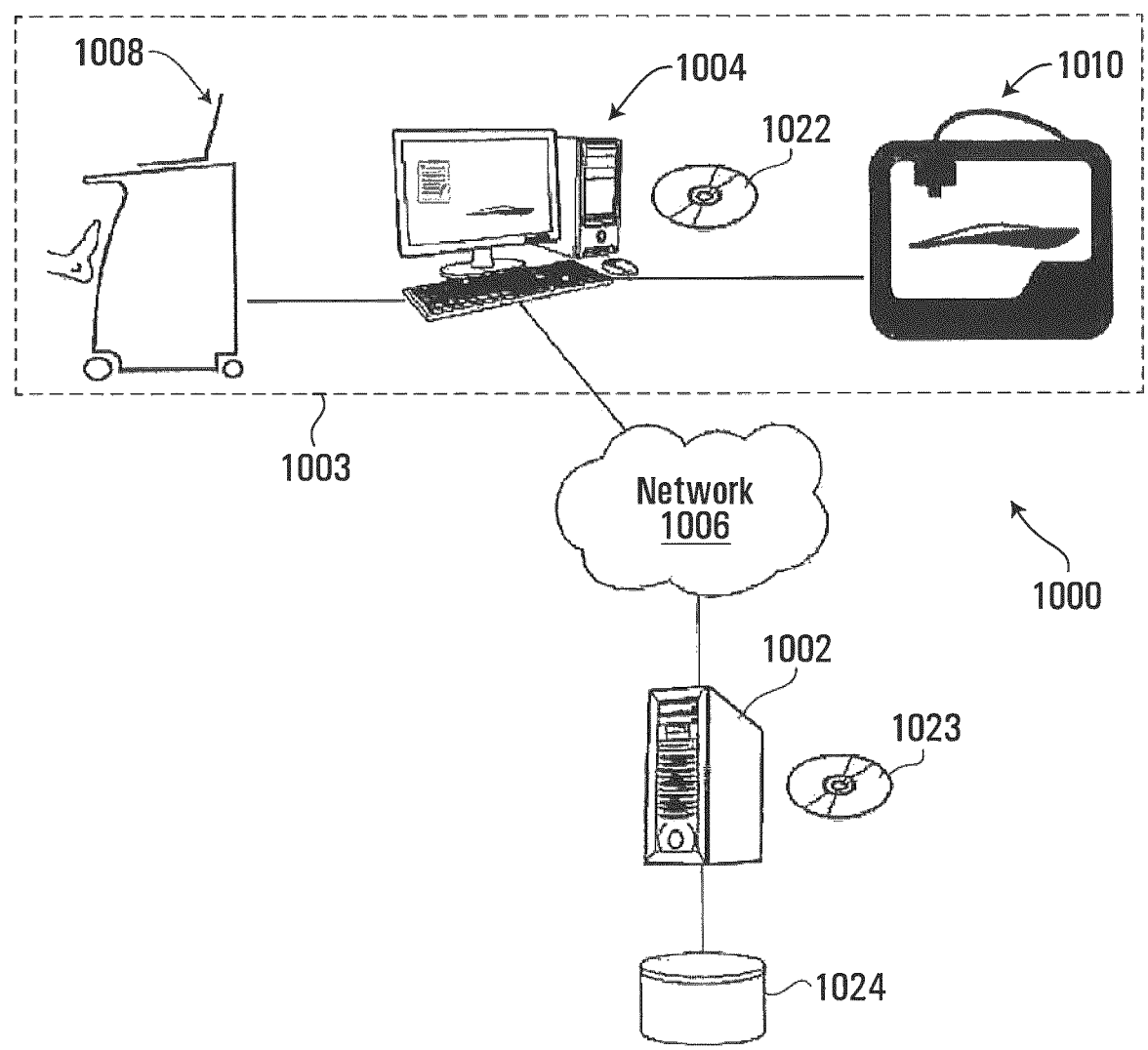
FIG. 11 is a schematic block diagram of a manufacturing system operable to design and fabricate custom foot orthotics.

In an embodiment, system 400 may be incorporated or integrated into a system for designing and fabricating 3D products, such as the system 1000 illustrated in FIG. 11.

Orthotics manufacturing system 1000 includes a server 1002 and at least one fabrication facility 1003. Fabrication facility includes a computing device 1004 connected to a scanning device 1008 and a printing device 1010. Server 1002 and computing device 1004 are connected to a computer network 1006. Computer network 1006 may be a wide-area network such as the internet, or may be a private or local area network, and may include wired or wireless access points.

Computing device 1004 may be a PC running a Microsoft Windows operating system or other suitable operating system such as Linux or OSX.

Scanning device 1008 is connected to computing device 1004, for example, by universal serial bus (USB) or over a network connection such as a wireless local area network (WLAN) connection or Ethernet, and is operable to measure the surface of a patient's foot and return to computing device 1004 three-dimensional coordinates of points on the surface. Scanning device 1008 may for example be a 3D laser scanner such as a ShapeGrabber SG502, structured light scanner such as a GOM ATOS Core 300 or photogrammetry device such as a PhotoModeler, produced by EOS Systems.

Printing device 1010 is connected to computing device 1004, for example, by USB or over a network connection such as WLAN or Ethernet, and is operable to receive instructions from computing device 1004 and fabricate foot orthotics in accordance with a model at computing device 1004. Printing device 1010 may for example be a three-dimensional printer such as a Makerbot Replicator, produced by MakerBot Industries LLC. Printing device 1010 may be capable of printing custom orthotic devices from feedstocks including, but not limited to nylon, polyester, nylon-polyester blend, polyethylene, polypropylene, acrylonitrile butadiene styrene, polylactic acid, polycarbonate, rubber, foam rubber, ethylene vinyl acetate, fiberglass, or carbon fiber graphite.

Figure 12:
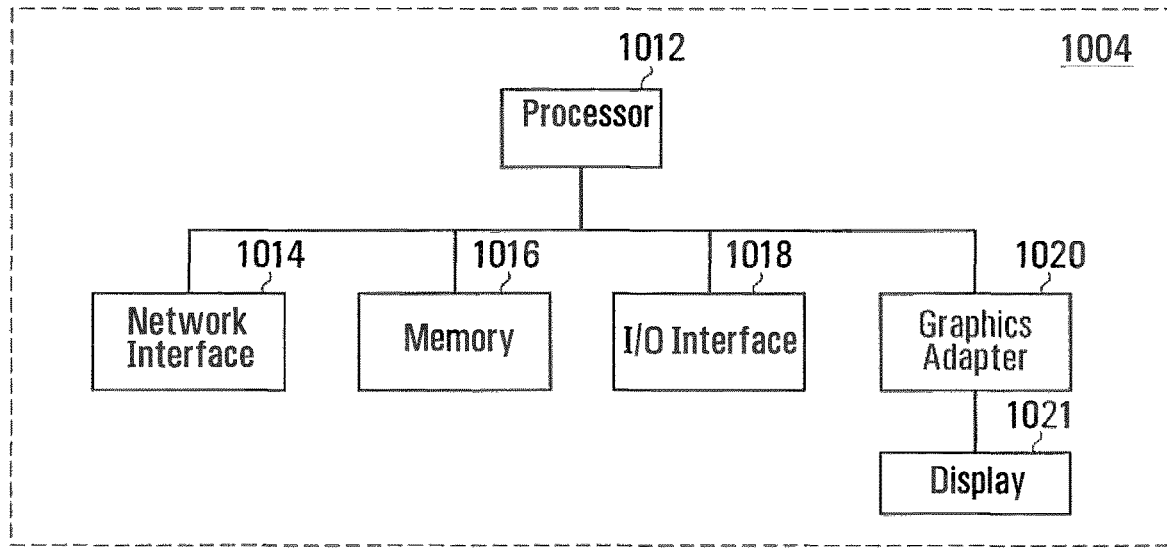
FIG. 12 is a schematic block diagram of a computing device of the system of FIG. 11.

FIG. 12 depicts components of computing device 1004 in greater detail. Computing device 1004 includes a processor 1012, a network interface 1014, a memory 1016, at least one I/O interface 1018, such as a USB controller or the like, and a graphics adapter 1020 for controlling an interconnected display 1021. Processor 1012 may be an Intel x86, PowerPC, ARM processor or the like. Network interface 1014 may, for example, be an Ethernet or WLAN adapter or cellular modem. Network interface 1014 interconnects computing device 1004 to network 1006 to send and receive data. Memory 1016 may be organized using a filesystem configured to store data structures as will be described in greater detail below.

Computing device 1004 executes application software loaded from a computer-readable medium 1022 (FIG. 11). As will be apparent, software may be loaded from a computer-readable medium local to computing device 1004, or may be from a computer-readable medium by way of a network connection. Loaded application software may be stored in memory 1016 and subsequently accessed from memory 1016.

Figure 13:
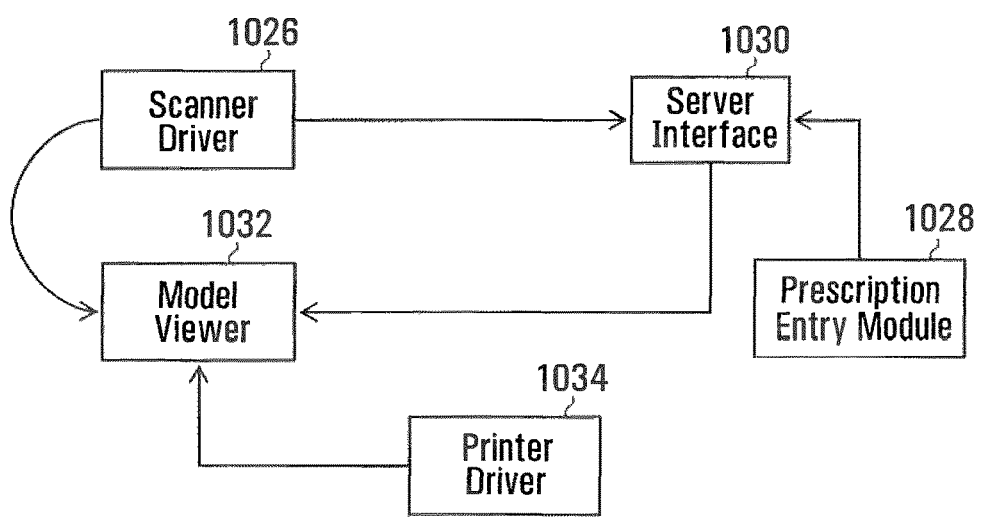
FIG. 13 is a block diagram of application software components at the computing device of FIG. 12.

FIG. 13 depicts components of application software at computing device 1004. Application software at computing device 1004 may include a scanner driver 1026, a prescription entry module 1028, a server interface module 1030, a model viewer 1032, and a printer driver 1034.

Scanner driver 1026 interfaces with scanning device 1008 by way of network interface 1014 or I/O interface 1018 to send instructions to and receive data from scanning device 1008. Specifically, scanner driver 1026 can be invoked from computing device 1004 to send instructions causing scanning device 1008 to scan a foot and return data containing a point cloud for the sole surface of the scanned foot, as described in U.S. patent application Ser. No. 14/638,911. The data structures of the stored data may, for example, be a delimited text file. Details may be as described as in U.S. patent application Ser. No. 14/638,911. Scanner driver 1026 is configured to output the data structure to server interface 1030 for provision to server 1002 over network interface 1014. The operation and use of system 1000 are also further detailed in U.S. patent application Ser. No. 14/638,911, the entire content of which is incorporated herein by reference.

Server interface 1030 may be configured to receive data structures from scanner driver 1026 and other data, and to send the data structures to server 1002 by way of network interface 1014. Server interface 1030 may also receive an orthotic model from server 1002.

The orthotic model may be received in a CAD file format, such as stereolithography (STL), initial graphics exchange specification (IGES) or standard for the exchange of product model data (STEP). Server interface module 1030 is configured to output the received orthotic model to model viewer 1032 for display.

Model viewer 1032 may be configured to receive an orthotic model from server interface module 1030 in a CAD file format and to display a representation of the solid model on interconnected display 1021 using graphics adapter 1020. Model viewer 1032 may also receive data structures and overlay a visual representation of the received data simultaneously with a solid model. Model viewer 1032 can rotate, pan, zoom and perform other transformations on the displayed representation, such that the solid model may be aligned with data points in the received data set to evaluate the fit of the foot orthotics.

Printer driver 1034 may be configured to be invoked by a user from solid model viewer 1032. Printer driver 1034 may be configured to read the CAD-format orthotic model, generate instructions for causing printing device 1010 to fabricate an orthotic device according to the CAD-format file, and provide those instructions to printing device 1010 by way of network interface 1014 or I/O interface 1018.

Server 1002 may be a computer running a Microsoft Windows operating system or other suitable operating system such as Linux or OSX.

Figure 14:
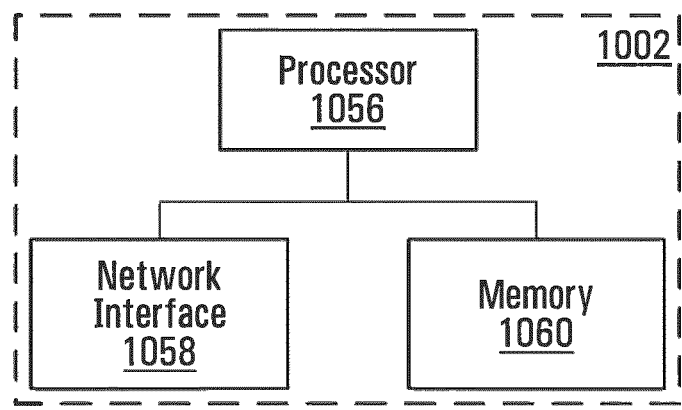
FIG. 14 is a schematic block diagram of the server of the system of FIG. 11.

FIG. 14 depicts components of server 1002 in greater detail. Server 1002 includes a processor 1056, a network interface 1058 and a memory 1060. Processor 1056 may be an Intel x86, PowerPC, ARM processor or the like. Network interface 1058 may, for example, be an Ethernet or WLAN adapter or cellular modem. Network interface 1058 interconnects server 1002 to network 1006 to send and receive data. Memory 1060 may be organized using a filesystem configured to store application software and data structures as will be described in greater detail below.

Server 1002 executes application software loaded from a computer-readable medium 1023 (see FIG. 11). As will be apparent, software may be loaded from a computer-readable medium local to server 1002, or may be from a computer-readable medium by way of a network connection. Loaded application software may be stored in memory 1060 and subsequently accessed from memory 1060.

Figure 15:
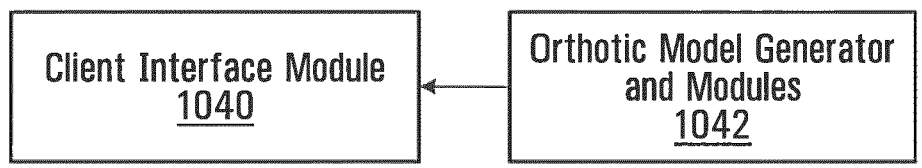
FIG. 15 is a block diagram of application software components at the server of FIG. 14.

As depicted in FIG. 15, application software at server 1002 may include a client interface module 1040, and a collection of modules for generating an orthotic model, for example as described in U.S. patent application Ser. No. 14/638,911.

Client interface module 1040 communicates with computing device 1004 to receive data structures for foot orthotics, and to return a three-dimensional model of an orthotic device in a CAD file format, once the model is constructed, for example as described in U.S. patent application Ser. No. 14/638,911.

A support structure as described herein may be added or attached to the orthotic model constructed by system 1000, according to an example process as described herein.

Server 1002 may include, or in communication with, a data storage device 1024 as depicted in FIG. 11, which may store one or more databases. The databases may include databases for foot orthotics, support structures, or user information, respectively. The entries in different databases may be cross-linked or associated as will be understood by those skilled in the art.

Figure 16:
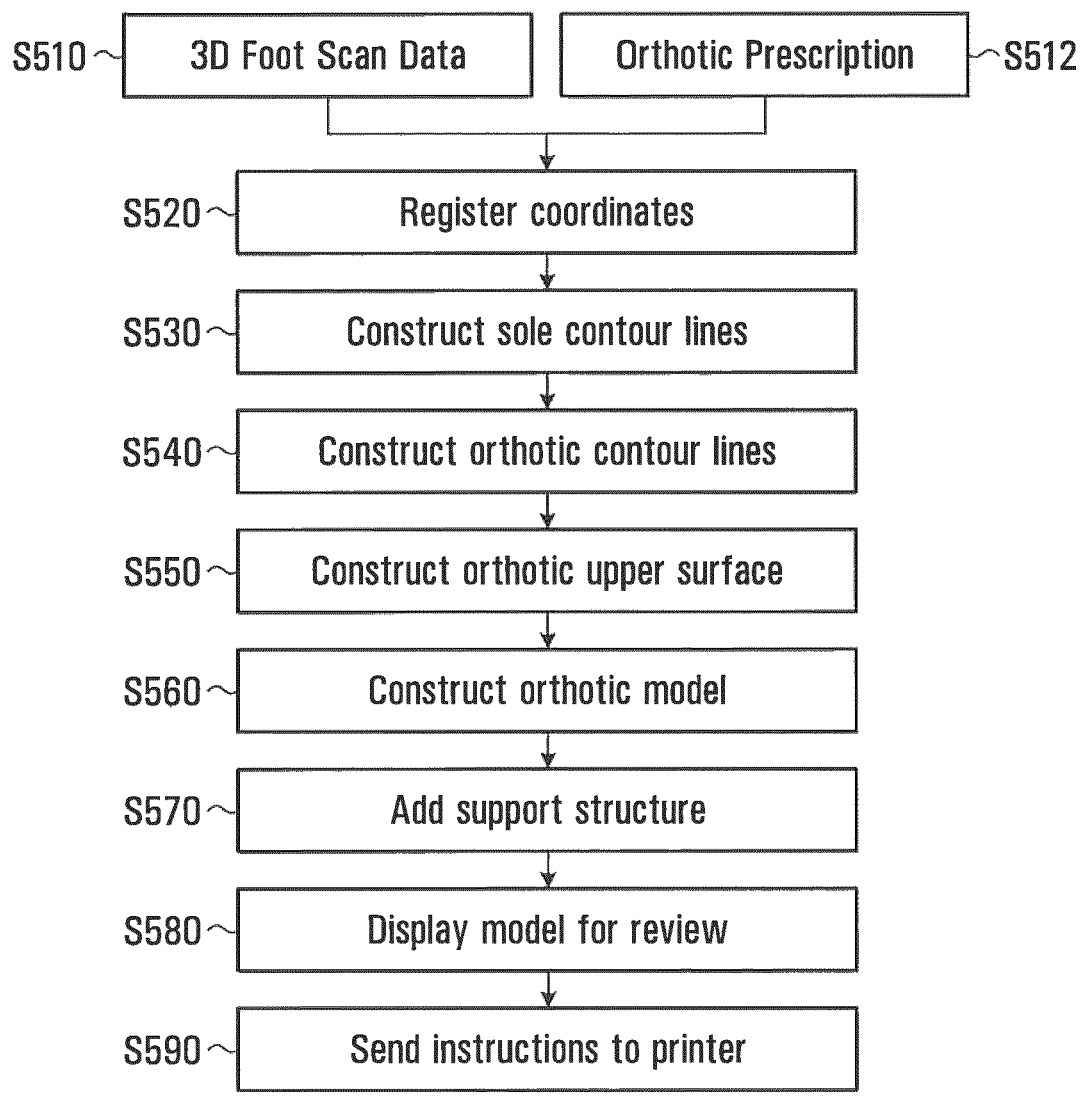
FIG. 16 is a flowchart of a process for constructing customized foot orthotics using the system FIG. 11.

FIG. 16 shows an example process S500 for adding a support structure to an orthotic model.

For the purpose of clarity, process S500 is described with reference only to a single foot (the "scanned foot"). However, it is to be understood that the described steps may be performed for each foot, serially or in parallel. Orthotic parameters and thus, the orthotic models described hereinafter may vary for each foot. Accordingly, a matching left-right pair may be constructed concurrently, but the resulting orthotics for each specific foot may differ.

At S510, data is acquired at fabrication facility 1003. Specifically, a specific foot may be scanned using scanning device 1008 to acquire a point cloud of measured points on at least the plantar surface of the foot. A data structure is constructed, which may include three-dimensional coordinates of points in a point cloud for the model. The coordinates may be stored in a data structure in an X-Y-Z coordinate system assigned by scanning device 1008. During scanning, the foot may be placed on a guide so that the X axis aligns approximately with the transverse direction of the foot, the Y axis aligns approximately with the longitudinal direction of the foot and the Z axis aligns approximately with the vertical direction. The generated data structure may be stored in memory 1016 of computing device 1004 (see FIG. 12).

Many foot orthotic devices extend only to the metatarsal heads of the wearer (not beneath the wearer's toes). Accordingly, during or after scanning, a scanner operator may review a representation of the scanned points on a display and demarcate the base of the toes. Points corresponding to the toes may then be discarded from the data structure, or an identifier may be appended to the data structure to identify points corresponding to the toes. Such points may then be disregarded during construction of an orthotic model. Identification of points corresponding to the toes may alternatively de done by automated processing of the scanned points.

At S512, the foot is examined, such as by a medical doctor to ascertain pathomechanical features of the foot. Such examination may include, for example, biomechanical examination and gait analysis. Based on the examination, desired properties of a custom orthotic device for the foot are identified. An operator at computing device 1004 interacts with a user interface (not separately shown but may be included in interface 1018) to input identification information and orthotic parameters corresponding to the desired properties of the orthotic device. The entered orthotic parameters may include material of the orthotics; shell rigidity; arch shape; heel cup depth; forefoot width; heel width; rearfoot posting type, angle and amount; heel lift; forefoot posting angle and amount, or the like. Optionally, a cover (e.g. a cushion) may be applied to an orthotic device, and the user interface may allow for entry of characteristics of the cover, such as thickness and color. The data entered to the user interface may be used to construct or populate a data structure for modifying the orthotic model, or forming a support structure, which may be stored in memory 1016 of computing device 104.

Data structures for the orthotic model and modification parameters may then be provided to server 1002 by way of network interface 1014 of computing device 104 (FIG. 12) and network interface 1058 of server 102 (FIG. 14). Point coordinates in the data structure for the orthotic model represent the shape of the plantar surface of the scanned foot. As will be apparent, the data structure could be directly used as a model for a surface of a foot device that fits the foot (i.e., conforms to the plantar surface). However, the contents of the data structure may also be modified to construct customized orthotics for various purposes.

At S520, the data structures may be registered in a suitable coordinate system, and further processing of the data structures may be performed, such as according to a process disclosed in U.S. patent application Ser. No. 14/638,911.

For example, at S530, the registered data structure may be processed to construct a plurality of sole contour lines corresponding to the shape of the scanned foot. At S540, orthotic contour lines may be constructed. The contour lines may be modified. The modifications to sole curves may be based on orthotic parameters provided by a user such as a doctor. In an example, the modifications may be based on arch height, heel cup depth, forefoot width, and rearfoot width parameters.

At S550, the orthotic contour lines may be used to construct a top orthotic surface model.

At S560, the orthotic contour lines may be used to construct a bottom orthotic surface model, thus forming a complete orthotic model.

At S570, a support structure, such as one illustrated in FIG. 9A to 10B may be added to the orthotic model, which may follow the process as illustrated in FIG. 8, and described above.

To briefly recap, a vertical wall structure may be added along the inner (medial) edge of the orthotic model. The vertical wall may extend transversely in the medial direction. A base plate may be added to an edge of the vertical wall, either to the medial edge or the lateral edge. The base plate may be substantially thicker than the vertical wall. Extension sections may be added to each end of the base plate for stabilization. The vertical wall, base plate and extension sections together form a support structure for supporting the orthotic device during fabrication (e.g. during 3D printing).

The digital orthotic model and the digital model for the support structure may be stored in a CAD file format, such as stereolithography (STL), initial graphics exchange specification (IGES) or standard for the exchange of product model data (STEP).

At S580, computing device 1004 receives the digital orthotic model and support structure in CAD-compatible format and model viewer 1032 may present a representation of the model on an interconnected display, such as display 1021, using graphics adapter 1020 (FIG. 12). The orthotic model may be presented in a user interface. The user interface may allow the orthotic model to be rotated, panned or zoomed so that an operator can align orthotic model 182 with foot image to assess fit.

The user interface may also display a print control. If the operator of computing device 1004 is satisfied with the modified orthotic model, the operator can activate the print control to send instructions to printing device 1010.

Alternatively, if the operator is not satisfied with the orthotic model, the operator may enter modified parameters corresponding to desired characteristics to be provided to server 1002 as a modified data structure. Optionally, modifications may be entered by way of the user interface presented by model viewer 1032. For example, modifications may be entered in a dialog. Alternatively, the operator may return to S510 and enter new parameters by way of another user interface at computing device 1004 (FIG. 5).

Optionally, on receiving the modified data structure, server 1002 may load the relevant registered point cloud data and resume process S500 beginning at S540, using the modified data structure. Alternatively, server 1002 may repeat process S500 from block S520.

At S590, model viewer 1032 may send the digital orthotic model and the digital model for support structure to printing device 1010 to cause printing device 1010 to fabricate a custom orthotic device in accordance with the orthotic model. Printer driver 1034 may translate the orthotic model from a CAD-file format to instructions in a format readable by printing device 1010.

As noted, a 3D printing device may be a fused deposition modelling (FDM) 3D printer. The printing device may deposit print material layer-by-layer through a print nozzle. The orthotic device may be built up in layers, beginning with the support structure according to the support structure digital model, followed by printing the orthotic device in a transverse direction, from its inner (medial) edge to its outer (lateral) edge. Each layer may approximately 0.2 mm thick, or have another thickness. After printing, the support structure may be removed from the completed orthotic device, for example by cutting or grinding.

Conveniently, the above-described system and process provides an opportunity for review of a prospective orthotic model prior to fabrication. For example, a user of system 1000 may be a podiatrist, who may examine and scan a foot and enter an initial set of orthotic parameters using user interface 1046 at computing device 1004. Server 1002 constructs custom orthotics for the foot according to the scanned model and the initial orthotic parameters and returns an orthotic model. The podiatrist may then evaluate the returned model by aligning and comparing it with the scanned foot. The orthotic parameters may then be altered as necessary and a new orthotic model is constructed based on the scanned foot and the revised parameters. If the new orthotic model is satisfactory, an orthotic device is fabricated based on the new orthotic model. Thus, a design may be quickly constructed and tested. In contrast, design by physical prototyping may be relatively slow and a design cannot be tested until a physical prototype is produced. The support structure may also be automatically added, or the operator may specific different parameters for the support depending on the particular situation.

As described above, server 1002 and fabrication facility 1003 are connected over a network 1006. Server 1002 and computing device 1004 are separate computers. However, in other embodiments, the functions of server 1002 and computing device 1004 may be carried out by a single computer. In such embodiments, data exchanges described above as occurring over network 1006 may occur between applications on a single machine, within memory.

It will be apparent that the components of fabrication facility 1003 need not be physically located together. In some embodiments, printing device 1010 or scanning device 1008 may be located remotely from computing device 1004. For example, scanning device 1008 and computing device 1004 may be located in an office and printing device 1010 may be remotely located at another facility. Correspondingly, support structure model may be generated at server 1002, computing device 1004, or printing device 1010, and may be modified at any location.

As described above, printing device 1010 is a 3D printer. However, other fabrication devices may be used. For example, printing device 110 could be any additive manufacturing device, or even a conventional manufacturing device such as a computer-numeric-controlled (CNC) mill. In such embodiments, printer driver 134 may be replaced with a module configured to control the specific fabrication device.

Figure 17A:
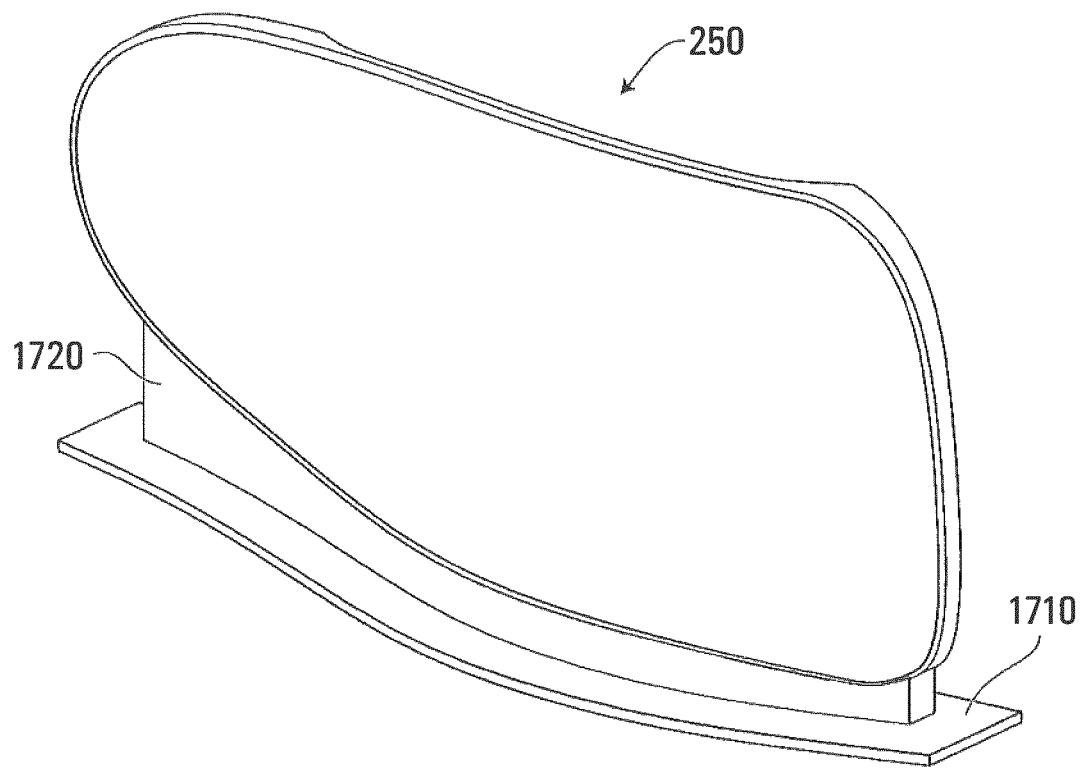
FIG. 17A is a perspective view of a foot orthotics and an example side support.
Figure 17B:
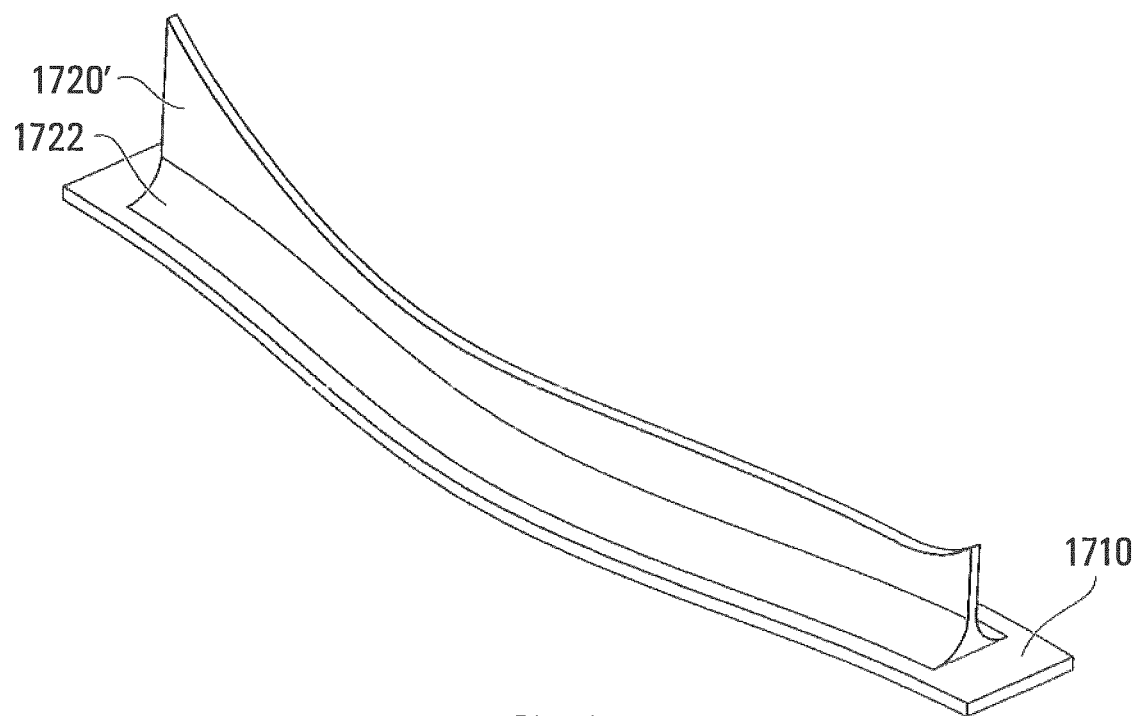
FIGS. 17B and 17C are perspective views of example side supports.
Figure 17C:
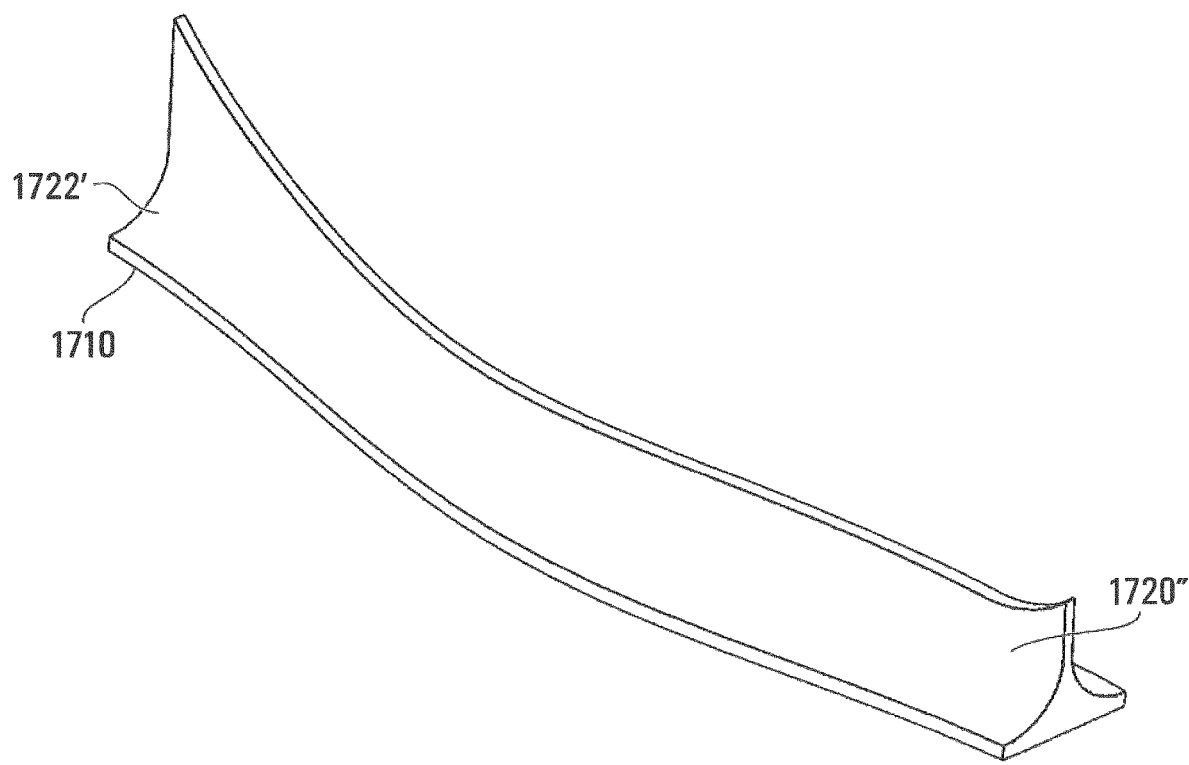

In an embodiment, a base plate 1710 in the side support may have a substantially uniform width along its length, as illustrated in FIG. 17A, when the width is sufficiently wide to provide adequate support and stability. The vertical wall 1720 in the side support may be similar to vertical wall 220. In an alternative embodiment, the vertical wall in the side support may have a gradually widened base portion, as illustrated in FIG. 17B, which depicts a vertical wall 1720' with a widened base portion 1722. As depicted in FIG. 17B, the bottom width of widened base portion 1722 may be narrower than the width of base plate 1710. In a further alternative embodiment, as illustrated in FIG. 17C, the bottom width of a widened base portion 1722' of a vertical wall 1720" may have the same width as that of base plate 1710. Base plate 1710 and vertical wall 1720, 1720', 1720" as depicted in FIGS. 17A, 17B, and 17C are curved in the horizontal (or lateral) direction, but the bottom surface (not shown) of base plate 1710 is flat and relatively straight to provide stable base support.

An embodiment of the disclosure relates to a process of constructing foot orthotics. In a typical process, a subject, such as a patient, visits a podiatrist or another medical professional at the professional's office such as a foot clinic. One or both feet of the patient can be examined and scanned using a suitable foot scanner in the clinic. The professional prepares prescription form containing patient information and foot orthotic parameters for custom foot orthotics for each scanned foot of the patient. A 3D image or model of the scanned foot and the corresponding prescription form are input into a user terminal at the clinic and communicated to an off-site server for constructing an orthotic model for each scanned foot. The server may construct the orthotic model as described herein. The orthotic model is then communicated from the server to the user terminal at the clinic. The medical professional may view the orthotic model on a computer display and may overlay (superimpose) the orthotic model with the scanned image of the corresponding foot to see how they fit. Based on this review, the medical professional may revise the orthotic prescription and send the revised prescription and the scanned model to the server to construct a revised orthotic model. Once the professional is satisfied with the orthotic model received from the server, the orthotic model may be loaded to an automated fabrication device such as a 3D printer to fabricate an orthotic device based on the orthotic model. Alternatively, the off-site server may be replaced with a local computing device located on site in the clinic. Conveniently, a podiatrist may have an opportunity to review and modify the orthotics before a physical orthotic device is fabricated. The patient may be able to receive and try the orthotic device within a short period of time, such as within one or two days. In some embodiments, a system including devices for scanning, model construction, and fabrication can be all provided at one location, and the location can be at or near the clinic. In some embodiments, a dedicated off-site server for model construction may be used to serve a large number of medical professionals or foot clinics at different locations. This may allow the users to share the costs of developing and maintaining more sophisticated modelling construction software, and allow the fabrication processes and products to be more conveniently standardized.

A further embodiment of the disclosure relates to a system for constructing foot orthotics. The system includes a data acquisition module or component for acquiring data structures representing a foot plantar surface or a contoured surface on a foot orthotics (a 3D orthotic model or an orthotic device), and representing orthotic parameters for constructing or modifying the foot orthotics. The system also includes a model construction component for electronically constructing or modifying 3D orthotic models. The model construction component may be configured and adapted to perform the functions and steps described above with reference to server 1002. The system further includes a fabrication component for fabricating foot orthotic devices based on 3D orthotic models constructed by the model construction component. The components of the system may be connected for inter-communication as needed. Each component of the system may be provided by a combination of hardware and software. One or more of components of the system may be integrated into one device or apparatus. The system may also be a distributed system. For example, one or more of the components of the system may be provided in separate devices and functions of a component may be performed by different devices at different locations. In particular, computing steps may be distributed over networked computers or devices. Some computing functions may be performed by hardware or software, or a combination of hardware and software. The system may be provided in part by a cloud computing technique. The system may require individual users of the system to pre-register, such as with a user management component of the system. The user may be assigned an identifier (ID) (e.g. a username) and a security code (e.g. a password). The scanned foot models and corresponding constructed orthotic models may be stored centrally or otherwise in association with information of the particular user who made the initial request and the particular patient of the user. The stored information may be retrievable at a later point in time. The stored information may also be analyzed to improve the modelling procedure (such as the modelling algorithm) or standardize the modelling procedure. The stored information may also be used to provide improvements to new orthotics for the same patient based on feedback from the user or patient with or without a new scan. The system may also provide a material or product ordering and delivering component for the users to order materials or components used to scan a foot or to make a foot orthotic device. For example, a user may order scanners, printers, printing materials or the like through the ordering component of the system. The system may provide a user interface for the users to conveniently interact with the system.

Other embodiments will be apparent, in which an initial computerized model of a contoured foot surface is received along with parameters for constructing a foot orthotic device and coordinates of points on the foot surface are adjusted based on curves derived from the parameters, the adjusted points defining a surface of a customized foot orthotic device, which can then be provided to a facility for fabrication.

It should be clarified that in this disclosure a point is considered to be "along" a line or a plane if the point is on the line or in the plane. A point may also be considered to be along a line if the point is not exactly on the line but is close to or near the line within a given distance, which may be pre-defined. In some cases, a particular pint may be considered to be along the line if the particular point is closer to the line than any other points under consideration. Similarly, a point or a line may be considered to be along or in a plane if the point or line is close to or near the plane within a given distance, which may be pre-defined. In some cases, a particular point or line may be considered to be in the plane if the particular point or line is closer to the plane than any other point or line under consideration. For example, as can be appreciated, the points in a point cloud, particularly a scanned 3D point cloud after re-registration in a different coordinate system, may not be perfectly aligned with the given coordinate axes or a reference surface. Therefore, some allowance may be required to account for the imperfect alignment. It may not be necessary in all cases for a point to be exactly on a line in order for the point to be included as a part of the line for fitting purposes. Similarly, it may not be necessary in all cases for a line to be exactly in a plane in order for the line to be included as a part of the plane for fitting purposes.

A fabrication facility may be as simple as a general purpose 3D printer, but may also be a dedicated installation with a special-purpose fabrication device or a sophisticated manufacturing plant.

Moreover, the disclosed design process can be tailored for computational efficiency. For example, applying orthotic parameters to curves prior to constructing an orthotic surface may limit the computational resources required for the design process. For at least some types of orthotic parameters, modifying an already-constructed surface, rather than the curves from which a surface is constructed, may be relatively more computationally intensive.

It will be understood that any range of values disclosed herein is intended to specifically include any intermediate value or sub-range within the given range, and all such intermediate values and sub-ranges are individually and specifically disclosed.

It will also be understood that the word "a" or "an" is intended to mean "one or more" or "at least one", and any singular form is intended to include plurals herein.

It will be further understood that the term "comprise", including any variation thereof, is intended to be open-ended and means "include, but not limited to," unless otherwise specifically indicated to the contrary.

When a list of items is given herein with an "or" before the last item, any one of the listed items or any suitable combination of two or more of the listed items may be selected and used.

Other modifications to the above-described embodiments are possible. The invention is therefore defined by the claims, which should be given a broad interpretation consistent with the description as a whole.

What is claimed is:

1. A method for additive fabrication of foot orthotics, comprising:

printing, in successive layers, a side support; and printing, in successive layers, a foot orthotics on the side support, wherein the foot orthotics comprises a top surface shaped to support a foot, a bottom surface opposite to the top surface, lateral side, a medial side, wherein the medial side comprises a side edge printed directly on top of the side support, and wherein the foot orthotics is supported only at the said edge of the medial side and is connected to the side support through the side edge, wherein the side support comprises a base plate and a vertical wall formed on the base plate, the vertical wall being continuous and having a thickness of 0.2 mm to 10 mm and a length of 50 mm to 300 mm, wherein the base plate comprises an elongated central section having a first width, and widened end sections having a second width wider than the first width for stabilizing the side support.

2. The method of claim 1, wherein the vertical wall is thinner than a thickness of the side edge of the foot orthotics.

3. The method of claim 1, wherein each one of the end sections is T-shaped, or generally circular-shaped.

4. The method of claim 1, wherein the side support is in continuous contact with the side edge.

5. The method of claim 1, wherein the side support and the foot orthotics are printed with a same material.

6. The method of claim 1, wherein successive layers are printed bottom-up.

7. The method of claim 1, wherein the printing comprises depositing a print material layer-by-layer.

8. The method of claim 1, wherein the side edge of the foot orthotics faces downward and the side support is directly below the side edge.

9. The method of claim 1, wherein the printing comprises fused deposition modeling.

10. A controller for controlling operation of an additive fabrication device, the controller comprising a processor and a memory, the memory storing thereon processor-executable-code, the code when executed by the processor, causes the additive fabrication device to:

print, in successive layers, a side support; and print, in successive layers, a foot orthotics on the side support, wherein the foot orthotics comprises a top surface shaped to support a foot, a bottom surface opposite to the top surface, a lateral side, and a medial side, wherein the medial side comprises a side edge printed directly on top of the side support, and wherein the foot orthotics is supported only at the side edge of the medial side and is connected to the side support through the side edge, wherein the side support comprises a base plate and a vertical wall formed on the base plate, the vertical wall being continuous and having a thickness of 0.2 mm to 10 mm and a length of 50 mm to 300 mm, wherein the base plate comprises an elongated central section having a first width, and widened end sections having a second width wider than the first width for stabilizing the side support.

11. The controller of claim 10, wherein the additive fabrication device comprises a three-dimensional printer.

12. A method of constructing a data structure for additive fabrication of foot orthotics, comprising:

obtaining a data structure comprising data representing a foot orthotics, the foot orthotics comprising an orthotic top surface, an opposite bottom surface, a lateral side, and a medial side, wherein the medial side has a side edge extending from the orthotic top surface to the bottom surface; and adding to the data structure additional data representing a side support connected to the foot orthotics only at the side edge of the medial side for supporting the foot orthotics through the side edge of the medial side during additive fabrication of the foot orthotics based on the data structure, wherein the side support comprises a base plate and a vertical wall formed on the base plate, the vertical wall being continuous and having a thickness of 0.2 mm to 10 mm and a length of 50 mm to 300 mm, wherein the base plate comprises an elongated central section having a first width, and widened end sections having a second width wider than the first width for stabilizing the side support.

13. The method of claim 12, wherein the adding comprises automatically adding the additional data to the data structure.

* * * * *